United States Patent
Dodge et al.

(10) Patent No.: US 9,329,131 B2
(45) Date of Patent: May 3, 2016

(54) METHOD OF ILLUMINATING ALGAE FOR ALGAE GROWTH

(75) Inventors: Corey Dodge, Cardiff, CA (US);
Graham Peers, Fort Collins, CO (US);
Jay McCarren, Cardiff, CA (US);
Miguel Olaizola, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 696 days.

(21) Appl. No.: 13/554,389

(22) Filed: Jul. 20, 2012

(65) Prior Publication Data

US 2013/0143255 A1 Jun. 6, 2013

Related U.S. Application Data

(60) Provisional application No. 61/510,214, filed on Jul. 21, 2011.

(51) Int. Cl.
*G06F 19/10* (2011.01)
*G01N 9/24* (2006.01)
*G01N 9/36* (2006.01)
*G01N 21/00* (2006.01)
*G01N 21/64* (2006.01)
*C12M 1/00* (2006.01)
*C12M 1/02* (2006.01)
*C12N 1/12* (2006.01)

(52) U.S. Cl.
CPC ........... *G01N 21/6486* (2013.01); *C12M 21/02* (2013.01); *C12M 41/06* (2013.01); *C12M 41/18* (2013.01); *C12N 1/12* (2013.01)

(58) Field of Classification Search
None
See application file for complete search history.

(56) References Cited

FOREIGN PATENT DOCUMENTS

WO 2006020177 2/2006

OTHER PUBLICATIONS

International Search Report with Written Opinion from PCT/2012/047578 dated May 14, 2013.
Nedbal et al., "A photobioreactor system for precision cultivation of photoautotrophic microorganisms and for high-content analysis of suspension dynamics", Biotechnology and Bioengineering, vol. 100, No. 5, Aug. 1, 2008.
Pruvost et al., "Simulation of Microalgae Growth in Limiting Light Conditions: Flow Effect", AIChE Journal, vol. 48, No. 5, p. 1109, 2002.
Sato et al., "Development of virtual photobioreactor for microalgae culture considering turbulent flow and flashing light effect"; Energy Conservation and Management, vol. 51, p. 1196, 2010.
Sastre et al., "Scale-down of microalgae cultivations in tubular photobioreactors—A conceptual 15 approach", Journal of Biotechnology, vol. 132, p. 127, 2007.
Lou et al., "Analyzing and Modeling of Photobioreactors by Combining First Principles of Physiology and Hydrology", Biotechnology and Bioengineering, vol. 85, p. 382, 2004.
James et al., "Modeling Algae Growth in an Open-Channel Raceway", J. Comp. Biol., 2010, vol. 17, pp. 895-906.
Perner-Nochta et al., "Simulations of light intensity variation in photobioreactors", J. Biotechnol., 2007, vol. 131, pp. 276-285.
Wu et al., "A model integrating fluid dynamics in the photosynthesis and photoinhibition process", Chem. Eng. Sci., 2001, Vo. 56, pp. 3527-3538.

*Primary Examiner* — Lori A Clow
(74) *Attorney, Agent, or Firm* — David M. Weisberg

(57) ABSTRACT

Systems and methods are provided for using a growth vessel to simulate algae growth and/or productivity in a reference environment, such as an open pond, a closed photobioreactor, or a hybrid system. Based on predicted algae sample trajectories in the reference environment, an illumination profile is developed. An algae sample in the growth vessel can then be exposed to the illumination profile under controlled conditions. Properties of algae in the reference environment can then be characterized based on the sample exposed to the illumination profile.

26 Claims, 8 Drawing Sheets

METHOD OF ILLUMINATING ALGAE FOR ALGAE GROWTH

CROSS-REFERENCE TO RELATED APPLICATIONS

This application claims benefit of priority to U.S. Provisional application 61/510,214 filed Jul. 21, 2011 entitled "Illumination Simulator for Algae Growth", which is incorporated by reference in its entirety.

FIELD OF THE INVENTION

Systems and methods are described for investigating algae properties.

BACKGROUND OF THE INVENTION

One potential source of biofuels is to generate molecules from algae that are suitable for making fuels. For example, algae, like plants, can generate lipid molecules. Some lipid molecules have a general structure and molecular weight suitable for making diesel fuel additives such as fatty acid methyl ester (FAME). It is also possible to refine certain algae lipids into conventional fuels or fuel blending stocks including gasoline, diesel, and jet fuel. However, many challenges remain in developing commercial scale production techniques for biofuels based on algae production.

One challenge in further investigating algae based biofuels is identifying algae that will grow effectively in different commercial environments. In a conventional commercial production setting, algae are grown in ponds or other bodies of water that are directly or indirectly impacted by a number of external environmental variables, such as sunlight and ambient temperature. By contrast, typical conventional laboratory settings for studying algae involve little or no exposure to external variables. This reduced exposure to external variables is based on a general desire to screen algae using fixed methods that, are repeatable over many test samples. However, conventional methods for introducing this repeatability can lead to laboratory conditions that are not representative of a commercial production environment.

Previous methods for designing photobioreactors have involved using three-dimensional computational modeling of the reaction environment in a photobioreactor. For example, a photobioreactor geometry can be used as a starting point for designing computational fluid dynamic simulations. Based on the photobioreactor geometry, the fluid flow within the photobioreactor can then be modeled to generate trajectories for the movement of algae within the photobioreactor. These simulated trajectories can then be used in combination with a light attenuation model, such as Beer's Law, and a photosynthesis model, to provide simulations that predict algae growth under various conditions. Examples of this type of work include "Simulation of Microalgae Growth in Limiting Light Conditions: Flow Effect" (Pruvost et al., AIChE Journal, Vol. 48, No. 5, p 1109, 2002); "Development of virtual photobioreactor for microalgae culture considering turbulent flow and flashing light effect" (Sato et al., Energy Conservation and Management, Vol. 51, p 1196, 2010); "Scale-down of microalgae cultivations in tubular photobioreactors—A conceptual approach" (Sastre et al., Journal of Biotechnology, Vol. 132, p 127, 2007); and Analyzing and Modeling of Photobioreactors by Combining First Principles of Physiology and Hydrology (Luo et al., Biotechnology and Bioengineering, Vol. 85, p 382, 2004).

In PCT International Application Publication WO/2006/020177, systems and methods are described for growing algae in a photobioreactor system. The methods include using computational fluid dynamics to calculate trajectories of algae particles in a photobioreactor. Models of photosynthetic behavior for algae are then used to determine desired amounts of light exposure for the algae in the photobioreactor. When algae are introduced into the photobioreactor, the schedule for light exposure is set based on the predictions from the photosynthesis model.

SUMMARY OF THE INVENTION

In one aspect, the invention provides methods for prediction of algal behavior in a reference environment, such as an outdoor pond or a large photobioreactor, based on growth of algae in a controlled growth environment. The methods can allow for determination and/or characterization of properties of an algae sample, as well as comparison of properties between algae samples, including algae samples composed of different algae strains.

In said methods, in order to model a desired reference environment, a particle trajectory can be calculated for a particle in a reference volume. Calculation of the particle trajectory includes calculation of at least a plurality of position values in the reference volume. The plurality of position values have associated times and include at least a depth value relative to a surface of the reference volume. Next, an illumination profile can be determined based on the particle trajectory. The illumination profile can be determined by obtaining an illumination intensity corresponding to the plurality of position values and associated times. This can result in an illumination profile corresponding to light intensity that an algae sample would encounter in the reference volume while traveling along the calculated trajectory. The illumination profile can then be used to expose an algae sample to light intensity based on the illumination profile. The algae sample can preferably have a volume less than the reference volume. A product of the optical density for the algae sample and a depth of the sample can be less than about 10.0 cm, is preferably less than about 8.0 cm or less than about 6.0 cm, and in some embodiments may be less than about 4.0 cm, for example, less than about 3 cm, about 2.5 cm, less than about 2 cm, about 1 cm, or less than about 1 cm. After exposing the algae sample to the illumination profile, at least one algal property for algae in the reference volume can be characterized based on a measured property of the algae sample exposed to the illumination profile in the vessel. The sample culturing period is used herein to refer to the time period in which an algae sample is exposed to light intensity according to an illumination profile or a continuous series of illumination profiles, and can be any period of time, but will typically be on the order of days or weeks.

Alternatively or in addition, during the culturing period, sample cultures can be allowed to attain an optical density of at least about 0.5, for example, at least about 1.0 or greater than 1.0. For example, the algae sample may not be maintained at a fixed optical density during the sample culturing period. Preferably the transmittance ($I/I_0$) of light through the algal sample during the sample culturing period can be greater than about 20% or greater than about 30%, and more preferably at least about 40%. The absorbance (($I_0-I)/I_0$) of the sample culture when it is exposed to an illumination profile cars reach levels greater than about 20% or higher than about 30% during the sample culturing period, and can reach levels as high as at least about 65%. For example, the highest absorbance value reached by an algae sample during the sample culturing period can be between about 20% and about 30%, or can be between about 30% and about 65%, for example between about 30% and about 60%, between about 40% and about 60%, or between about 40% and about 55%.

Further, in some practices of the invention, the illumination profile can be modified during the sample culturing period based on optical density measurements made during the sample culturing period. For example, in methods where the sample culture is allowed to increase in optical density, the illumination profile can be modified to incorporate attenuation calculations based on updated optical density values. For example, the optical density of an algae sample can be measured one or more times during the sample culturing period to obtain updated optical densities that are used to modify the illumination profile to which the algae samples are exposed as the sample culturing period continues.

The methods above can also allow for comparison of properties of multiple algae samples. For example, two algae samples can be exposed to an illumination profile. The algae samples can be exposed to the illumination profile in different vessels, or the same vessel can be used to consecutively expose the algae samples. One or more properties of the algae samples can be measured, such as, for example, productivity (biomass accumulation), a photosynthetic property, gene expression, a biochemical property, or biomolecule production. One or more environmental conditions can optionally be varied while exposing the samples to the illumination profile. Properties of the two algae samples after exposure can then be characterized to determine the comparative impact of varying environmental conditions on the growth or productivity of the algae samples.

In still another aspect, systems for simulating the growth environment of a reference system are provided. Such systems can allow for exposure of an algae sample to an illumination profile under controlled conditions. A system can typically include a vessel having a depth of about 10 cm or less, for example, about 4 cm or less, about 2 cm or less, or 1 cm or less, and a cross-sectional area, the depth and the cross-sectional area corresponding to a vessel volume of less than about 5 liters, for example, less than or equal to about 1 L or less than or equal to 500 ml. The vessel can be used in conjunction with a plurality of light sources positioned so that emitted light is incident on a vessel surface having an area corresponding to the cross-sectional area. Light from the plurality of light sources can be focused or otherwise directed toward the cross-sectional area using a plurality of lenses positioned to increase the percentage of emitted light that is incident on the vessel surface. It is noted that the dimension corresponding to the depth of the vessel does not need to correspond to the direction of gravitational pull. Instead, the vessel can be oriented in any manner that is convenient for allowing the plurality of light sources to be incident on the cross-sectional area. A system can further typically include a memory for storing at least a portion of an illumination profile and a processor. The processor can control at least one power source for the plurality of light sources based on the stored at least a portion of an illumination profile. This can allow the illumination profile to be replicated by the plurality of light sources. Preferably, the plurality of light sources and the plurality of lenses can be positioned to be capable of delivering at least about 1000 $\mu E/m^2/s$ PAR of illumination to the cross-sectional area of the vessel surface.

DETAILED DESCRIPTION OF THE EMBODIMENTS

Overview

Figure 1:
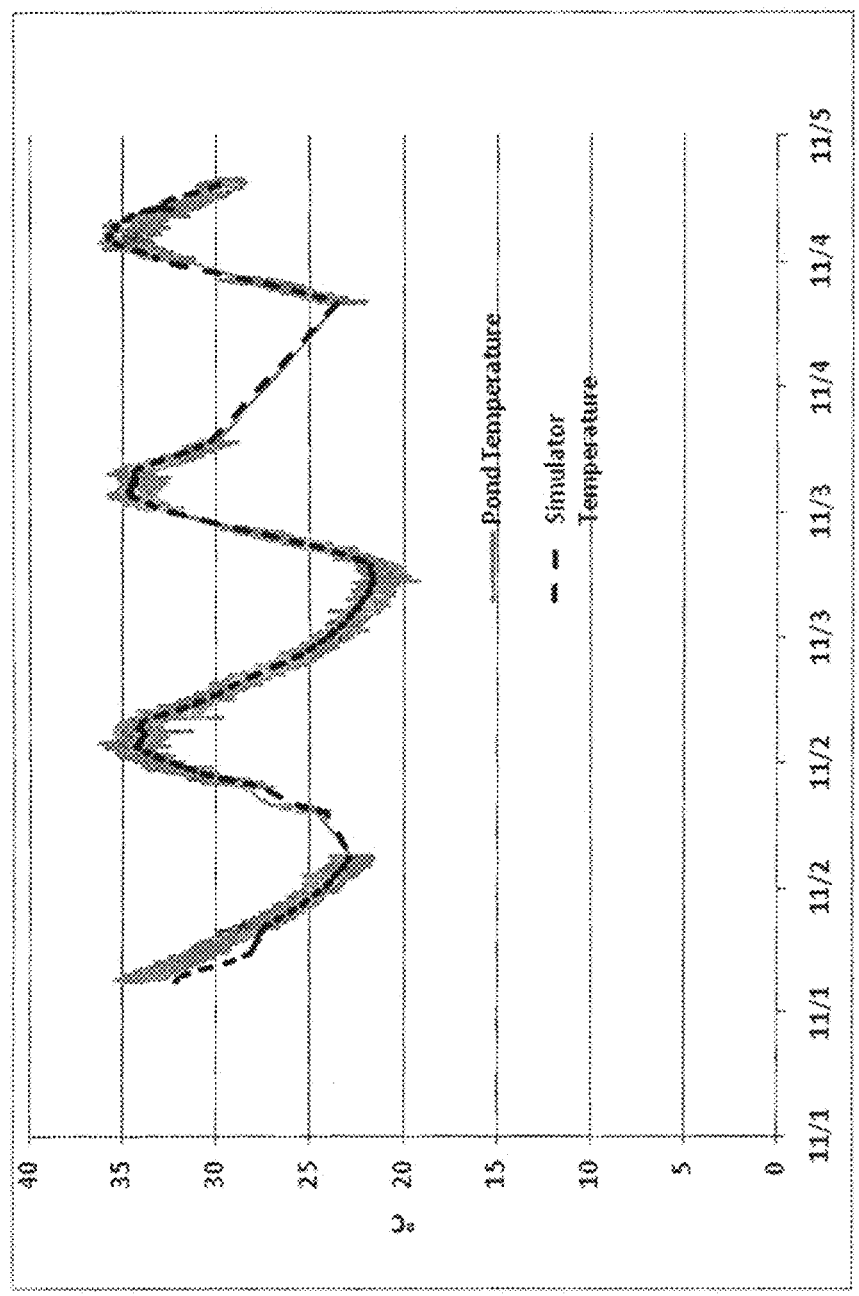
FIGS. 1-4 show data comparing the performance of a system according to the invention with raceway pond data.

Systems and methods are provided for growing algae under conditions selected to represent a growth environment in a reference geometry, such as conditions corresponding to a raceway pond. The simulated conditions can be derived in whole or in part from modeling particle trajectories in a reference geometry (such as an open pond, a closed photobioreactor, or a hybrid system) using computational fluid dynamics. Alternatively, fluid flows in an existing reference geometry can be measured, and the measured flow field can be used for generating random trajectories for a simulated particle in the reference geometry. In combination with a light attenuation model, and preferably in combination with a model of light incidence, the particle trajectories can then be used to determine a light exposure or illumination profile for algae. Optionally, the model can be supplemented with model information and/or measured information regarding any variable that may change in space or time during cultivation in a reference environment. Examples of supplemental model and/or measured information include the optical density of the culture in the test vessel, the temperature of the reference environment, the $CO_2$ content and/or pH of the reference environment, and the $O_2$ content of the reference environment. The algae can then be placed in a tank or vessel and exposed to light based on the illumination profile as well as model environmental conditions such as temperature. Alternatively, conditions such as temperature can be fixed, such as by placing the vessel in a temperature bath. Alternatively, one or more variables can be set initially and then allowed to vary based on the ongoing growth reactions in the vessel. The inventive systems and methods allow for growth and/or maintenance of algae in a test vessel under conditions that are selected to model a larger scale reference environment, such as a photobioreactor, a raceway pond, or any other commercial production environment. For example, instead of using a photosynthesis model, algae can be exposed to an illumination profile under representative conditions in a test vessel. This can allow for algae growth or lipid production under the illumination profile, followed by measurement of the resulting algae or algal products. The methods can be used to evaluate algal properties or production levels in a scaled down system and can be used to screen strains and growth conditions in a convenient and efficient format that is predictive of large scale cultures.

Predicting Trajectories and Creating Illumination Profiles

As an initial step, in any of the systems and methods, computational fluid dynamics (CFD) calculations can be used to predict a trajectory for an algae cell as it moves through a growth environment. The growth environment being simulated typically corresponds to a photobioreactor, a raceway pond, or any other type of closed, open, or hybrid reaction environment for growing algae. Various computational fluid dynamics calculation programs are available, such as Fluent from Ansys, Inc. of Canonsburg, Pa.

The geometry of the growth environment can be created within the computational fluid dynamics program. The volume in the geometry can then be divided into a mesh or grid of volume elements to allow for calculation of a flow within the geometry of the growth environment. A solution can then be calculated for the flow within the geometry, or a flow pattern can be calculated to incorporate an energy-source, such as a paddle wheel for a raceway pond geometry. In some embodiments, a steady state solution for the flow can be sufficient even though the corresponding system being modeled includes a discontinuous energy source.

After developing a flow solution for the geometry, test particles representing an algae cell can be introduced into the modeled flow pattern. The trajectories or traces of test particles can be tracked and recorded as the test particles travel through the geometry. For example, if the reference geometry being modeled represents a raceway pond, particle trajectories or traces can be modeled that correspond to one circuit for a particle around the pond. Thus, each individual trajectory can correspond roughly to a period of time. The period of time can be a few minutes, about 0.5 hours, about an hour, about 2.5 hours, or any other period of time that is desired and/or characteristic of the system being modeled. A particle trace or trajectory can represent a series of discrete location values, or the trajectory can be a continuous position function. A particle trajectory includes at least a depth value for a particle as a function of time. Typically, a particle trajectory can also include lateral coordinates indicating a location within a reference geometry. However, the coordinates in a particle trajectory do not necessarily have to be expressed as Cartesian coordinates. For example, in the case of circular or annular reference geometries, it may be more convenient to use coordinates corresponding to a depth, a radial position, and an angular position. It is noted that, even if a coordinate system does not explicitly have a coordinate expressing a depth relative to a surface in the geometry that is exposed to incident illumination, it is sufficient for purposes of this invention that the depth relative to a surface in the geometry can be derived from the position coordinates. Thus, any set of information for a trajectory that can provide, directly or indirectly, a depth coordinate can be considered equivalent to explicitly having a depth coordinate for the trajectory.

The process for modeling a trajectory or trace can be repeated any convenient number of times in order to generate a library of trajectories, which can be on the order of at least about 100 trajectories, for example at least about 1,000 or at least about 10,000. The trajectories from the library can then be selected for use in determining illumination exposure conditions for algae. It is possible to have a person select one or more representative trajectories, based on any convenient criteria. A more convenient way to select trajectories can be to use random selection. If a sufficient number of trajectories are used for data selection, the effects of any non-representative trajectories within the trajectory library should be mitigated. In some embodiments, it is desirable to develop an illumination profile that is longer than a single trajectory or trace. For example, a single particle trace may correspond to an hour or several hours, while an illumination profile can be desired for a longer time period, such as 72 hours or several weeks. In this example, a plurality of particle traces can be selected at random and chained together to form a longer particle trajectory corresponding to the desired time period.

For an existing reference system, in any of the systems and methods, an alternative to computational modeling can be to measure fluid velocities in the reference system. The measured velocities can be used to develop a fluid flow field model for the reference system. Using methods similar to a CFD calculation, the measured fluid flow field can be used to generate random particle trajectories or traces. In one embodiment, a more accurate computational model can be created by tuning model variables, and validating predicted results, with measured fluid velocities in the reference system.

Based on a particle trajectory of a given length of time, an illumination profile can be created that corresponds to the trajectory. An illumination profile represents the actual light an algae cell should receive if the algae cell were to follow the predicted trajectory in the reference growth system, e.g., an open, closed, or hybrid pond or bioreactor. The illumination profile can take into account several factors. First, the characteristics of the source of illumination (e.g., intensity, duration, and wavelength) should be considered. In some embodiments, the goal is to model a pond or other body of water that is exposed to sunlight. In such embodiments, the sunlight can be directly incident on the surface of the body of water, or the sunlight can be attenuated prior to reaching the water. This could represent, for example, a small pond located within a greenhouse type structure. Alternatively, the illumination profile can model an artificial source of light, such as the artificial light sources used in some photobioreactors. The terms "artificial light" or "artificial source of light" are used here to refer to any type of light different from sunlight. Thus, artificial light can include incandescent sources, fluorescent sources, light emitting diode sources, or any other convenient source for generating light. Still another option can be to model a structure surrounding a body of water that allows sunlight to enter, but that can also include artificial sources of light.

Based on the source of light, the illumination incident on the surface of the body of water in the reference geometry can be determined during the time period for the trajectory. As an example, consider a trajectory representing algae movement through a pond during daylight hours on a day having 12 hours of daylight. During the course of the day, varying amounts of sunlight will be incident on the surface of the pond. The incident sunlight on the pond can be represented in any convenient manner. One option can be to determine a maximum amount of light that will be incident on the body of water, and then express the incident light at other times as a fraction of the maximum incident light.

In an example involving a pond exposed to sunlight, an illustrative maximum sunlight intensity on a pond surface is about 2000 $\mu E/m^2/s$ of photosynthetically active radiance (PAR). Photosynthetically active radiance refers to light intensity between about 400 nm and about 700 nm, which corresponds to light intensity that participates in typical photosynthetic processes. This number could vary depending on a variety of factors, such as the time of year, a latitude selected for the model pond, or an expected amount of cloud cover. In alternative embodiments, still other factors could be accounted for in determining the amount of light incident on the surface of a body of water. Accordingly, in various embodiments, the maximum sunlight intensity can be selected to be at least about 400 $\mu E/m^2/s$ PAR, for example at least about 800 $\mu E/m^2/s$ PAR, at least about 1000 $\mu E/m^2/s$ PAR, or at least about 1500 $\mu E/m^2/s$ PAR. Additionally or alternatively, the maximum sunlight intensity can be selected to be about 2400 µE/m²/s PAR or less, for example about 2000 µE/m²/s PAR or less or about 1500 µE/m²/s PAR or less. Based on the selected maximum, the illumination incident on the pond surface during the course of the day can be calculated based on the angle of the sun. The incident illumination can optionally be calculated as a continuous function, to reflect the continuous nature of the change in sunlight intensity over the course of a day. Alternatively, the incident illumination can be calculated in a discreet manner, such as assigning an average illumination intensity for each 6 second period, each 10 second period, each 1 minute period, each 10 minute period, each 15 minute period, and/or for any other convenient period of time.

The above example relates to determining intensity for a pond exposed to sunlight. In other embodiments, at least a portion of the light incident on a body of water can be artificial light. In such embodiments, the amount of light incident on the body of water can be calculated based on factors such as the output illumination intensity of the light sources and the percentage of the source illumination that contacts the surface of the body of water.

Based on the amount of light incident on the surface of a body of water, an illumination profile for algae can be determined by using the trajectory for the algae to calculate an amount of light attenuation for the incident light. As algae move through a body of water, the location of the algae relative to the surface of the body of water will typically vary. Due to light attenuation, the amount of illumination the algae are actually exposed to will typically vary. When the algae are closer to a surface where light is incident, the algae will be exposed to a greater amount of incident light. When the algae are at a greater distance from a surface where light is incident, the amount of light intensity reaching the algae will be reduced.

The attenuation of light as it passes through a body of water can be expressed as an optical density for the algae-containing water. One way of expressing optical density can be as a percentage of light attenuation per centimeter of depth for the water. Optical density through the sample, or absorbance ($A_\lambda$), is inversely related to the transmittance of light through the sample: $A_\lambda = \log_{10}(I_0/I)$, where $I_0$ is the incident light intensity and $I$ is the intensity of the light after it passes through the sample, and transmittance=$(I/I_0)$, often expressed as a percentage.

When determining an illumination profile, the optical density of the algae-containing water can be set to any convenient value. Optical density (OD) is often used as a correlate of algal cell concentrations, where an optical density for determining algal cell concentration can be determined at wavelength outside the PAR range, for example, at 730 nm or 750 nm, so that differences in the amount of photosynthetic pigments of the cells (which can vary, for example, with growth conditions) do not improperly influence estimates of cell concentration. Depending on the type of algae, an optical density of 1.0 (for example, at 730 nm) can correspond to a biomass concentration in water of from about 0.3 g/liter to about 0.5 g/liter. Typical maximum optical density values for a raceway containing algae in an aqueous media range from about 0.5 to about 0.75, but in some instances may be higher; for example, optical densities in raceway ponds may be greater than 1.0, depending on factors such as algae concentration and absorptivity, but any optical density value can be selected for a simulator culture that models a desired growth environment.

The optical density for a body of algae-containing water can correspond to an absorption coefficient in Beer's Law. As described above, optical density-corresponds an amount of absorption per centimeter (or another convenient length unit). Based on an optical density (or absorption coefficient) $\alpha$ and a path length L, Beer's law can be written as:

$$\alpha L = -\log_{10}(I_L/I_0) = \epsilon L c$$

where $\alpha L$ is the absorbance ($A_\lambda$) of the culture at a particular wavelength, $I_0$ represents the intensity of light incident at the surface, and $I_L$ represents the intensity of light at distance L from the surface. If additional information is available regarding the types of algae present in the water, it may be possible to calculate the absorption coefficient or optical density $\alpha$ at a wavelength of the incident light (i.e., a PAR wavelength) based on the concentration c of algae in the water and the molar absorptivity or extinction coefficient, $\epsilon$, of the algae at the incident light wavelength. The extinction coefficient of an algal strain can be determined by measuring light intensity at various depths of an algal culture, such as a pond culture, where the concentration of the algae and the intensity of incident light are known. The extinction coefficient of a strain (measured at a PAR wavelength) may vary over time in culture, as the strain can adapt to culture conditions by increasing or decreasing pigments that absorb PAR. Extinction coefficients may therefore optionally be determined for an algal strain at various times during culturing, for example, extinction coefficients can be measured daily for a period of several days, a week, or several weeks, to provide extinction coefficients for the strain at various stages of culturing of the strain. One or more extinction coefficients obtained for an algal strain can be used to generate the illumination profile, where the illumination profile varies over the culture period at least partly to take into account the variation in the extinction coefficient over time in a culture. Extinction coefficients used to generate an illumination profile for a given algal strain can also or alternatively be extinction coefficients obtained from one or more culture measurements of a similar algal strain. For example, illumination profiles can be generated for a given strain based on one or more extinction coefficients calculated for one or more strains of the same algal taxon, such as the same algal family, order, class, and/or genus.

For convenience, in making an illumination profile, a single optical density value can be used for all incident wavelengths of light. Of course, the amount of light attenuation could be refined by using an optical density function that provided a wavelength dependent value for optical density. In some embodiments, the optical density value used to calculate attenuation can change over time, to reflect or model changes in the density of algae in the body of water. For an existing body of water or reference geometry, the optical density under various conditions can be measured. Alternatively, for any reference geometry, the optical density can be selected to have a desired value, such as an optical density corresponding to a desired concentration of algae in the body of water.

Based on the optical density for the algae-containing water, the amount of light intensity reaching algae at a given point in a trajectory can be calculated in order to provide an illumination profile for the algae. The trajectory can provide the depth of the algae in the water. The amount of light incident on the surface of the water can be determined or modeled based on the light source(s). The optical density can provide the information needed to determine the intensity of light reaching the algae based on the intensity of light at the water surface. Based on Beer's law, these values can generate the light incident on the algae at each point in the trajectory. This series of incident light values corresponds to an illumination profile (or illumination history) for the algae.

In using simulator cultures to model a reference algal culture, in some modes of operation, the density of the simulator algal cultures can be maintained at or below a certain limit, which can be represented, for example, by an optical density (which can be optical density at 730 nm, believed to correlate with cell concentration) to minimize light attenuation through the sample cultures. For example, the desired optical density can be maintained at about 0.6 or less, for example about 0.5 or less, about 0.3 or less, about 0.2 or less, about 0.1, or about 0.1 or less.

Alternatively, in some methods of practicing the invention, the optical density of a simulator culture may be allowed to increase during the sample culturing period. That is, the algae sample may exposed to an illumination profile without dilution of the sample culture during the sample culturing period. For example, an algae sample during a simulation run or sample culturing period can be grown to an optical density of greater than about 0.2, for example, greater than about 0.5, greater than about 1.0, greater than about 1.5, about 2.0, or greater than about 2.0; for example, an algae sample can reach an optical density of between about 0.5 and about 1.0, between about 1.0 and about 1.5, between about 1.5 and about 2.0, or between about 2.0 and about 2.5 during the sample culturing period. In these methods, a simulator culture may be monitored for optical density regularly, such as, for example, daily, during the sample culturing period, and an updated optical density of the simulator culture can be programmed into the simulator system to modify the illumination profile, taking into account the new optical density value. In this way, the simulator sample culture can provide an updated value or values for optical density for the culture as the optical density increases with time, such that the light attenuation model (and illumination profile) can be modified to reflect increases in culture density that occur in a growth environment. Thus, in some examples the algae sample can, during the sample culturing period, be exposed to a series of illumination profiles, as the initial illumination profile is modified to incorporate successive updated optical densities into light attenuation calculations that affect the light intensity values of the illumination profile. The algae sample can thus be exposed to one or more modified illumination profiles, where the modified illumination profiles are based on optical densities of the culture over the sample culturing period.

Testing Apparatus—Algae Growth Vessel

In order to expose algae to a desired illumination profile, the algae can be placed in a suitable tank or vessel. In addition to allowing for exposure of algae to illumination, the growth vessel can also allow for control of one or more additional variables related to algae growth.

One set of considerations for the growth vessel can be the size and shape of the vessel. The size and shape of the vessel should be selected so that the vessel can hold a sufficient volume of algae to allow for desired characterization or testing of the algae. Additionally, the vessel can have a shape that reduces or mitigates light intensity attenuation for the algae inside the vessel.

In order to reduce or mitigate light attenuation, the algae-containing water sample within the growth vessel can have a gauge dimension, which can be referred to as a water depth or sample depth, of about a few centimeters or less, such as less than about 10 cm, and preferably less than about 8 cm, for example, less than about 6 cm, less than about 4 cm, less than about 3 cm, between about 2 cm and about 3 cm, about 2 cm, between about 1 cm and about 2 cm, or about 1 centimeter. At a depth of about 1 centimeter, an algae-containing water sample in the vessel can have an optical density of up to about 0.1 or 0.2 while still allowing the algae in the vessel to experience a light intensity comparable to the incident intensity. At a water or sample depth of about 1 centimeter, optical densities up to about 0.5 may also be suitable while still providing a growth environment comparable to a body of water that is being modeled. At a water or sample depth of about 2.5 cm or less, such as about 2 cm or less, optical densities up to about 2.5, for example, up to about 2.0, up to about 1.5, up to about 1.0, or up to about 0.6, may also be suitable. Using methods provided herein, sample cultures having depth dimensions of up to at least about 2 cm and having optical densities greater than 0.6 or greater than about 1.0 can provide a growth environment that results in biomass or biomolecule productivities comparable to a reference body of water that is being modeled. For example, in some instances, algal cultures in the growth vessel having a depth of about 2 cm or less may reach optical densities of greater than 0.2, for example, greater than 0.5, greater than 1.0, between about 1.0 and about 1.5, greater than 1.5, between about 1.5 and about 2.0, or at least about 2.0, during the course of the growth experiment. In some examples, the algal sample may not be diluted during the culturing period.

Note that the "depth" dimension of the growth vessel does not have to be oriented to match the direction of gravitational pull. Instead, the depth or gauge dimension is defined as a direction that is approximately perpendicular to a surface of the water that receives the majority of incident light intensity. For an outdoor pond system, the depth dimension will often coincide with the direction of gravitational pull, but in a closed photobioreactor type system the surface of the water that receives incident light can have any desired orientation relative to gravity. Note that in many cases it can be desirable to use an algae-containing water sample with a sample volume that is less than the volume of the growth vessel. For a growth, vessel where the "depth" dimension is roughly aligned with the direction of gravitational pull, the difference between the sample volume and growth vessel volume can result in the depth dimension for the interior of the growth vessel being different from the sample depth dimension for the water sample within the vessel.

In other embodiments, other depths (or gauge dimensions) for the algal culture sample in the growth vessel can be selected, and a corresponding depth can be selected for the interior of the growth vessel. For example, the water or sample depth can be selected so that, light attenuation at a desired algae concentration will be acceptable. The water in the growth vessel can have a depth of about 1 cm or less, for example about 2 cm or less, about 5 cm or less, about 8 cm or less, or about 10 cm or less. Additionally or alternatively, the water can have a depth of at least about 0.1 era, for example at least about 0.2 cm, at least about 0.5 cm, at least, about 1 cm, at least about 2 cm, or at least about 4 cm, at least about 6 cm, at least about 8 cm, about 10 cm, or at least about 10 cm.

Another way of selecting a depth for the growth vessel (or depth of the sample in the growth vessel) can be based on the product of the vessel (sample) depth and the expected optical densities for algae solutions that will be studied in the growth vessel. For example, for an algae sample with a depth (gauge dimension) of 0.5 cm and an optical density of 0.3, the product of the sample depth and optical density is 0.15 cm. In various embodiments, the product of the water or sample depth (measured in centimeters) and optical density of the algae sample in the vessel can be about 1.0 cm or less, for example, about 0.75 cm or less or about 0.5 cm or less. In further examples, the product of the water or sample depth in the simulator vessels and the optical density of the algae sample in the vessel can be about 10 cm or less, for example, about 8 cm or less, about 6 cm or less, about 4 cm or less, or about 2 cm or less. In such instances, the product of the water or sample depth (measured in centimeters) and optical density of the algae sample in the vessel can be greater than about 1.0 cm, and may be between about 1.0 cm and 2.0 cm, between about 2.0 cm and about 2.5 cm, between about 3.0 cm and about 3.5 cm, between about 3.0 cm and about 4.0 cm, at least about 4.0 cm, or between about 4.0 cm and about 6.0 cm. The product of the sample depth and optical density can be evaluated based on the initial optical density of an algae sample, or the product of the sample depth and optical density can be used as a maximum value for any time during illumination of an algae sample.

Alternatively, the algal sample depth can be selected such that throughout the sample culturing period the percent transmittance $((I/I_0) \times 100\%)$ at a PAR wavelength of the algal culture can be at least 35%, for example, at least 40%, at least 45%, or at least about 50%. Alternatively or in addition, the algal sample depth can be selected such that throughout the sample culturing period the percent absorbance $((I_0-I/I_0) \times 100\%)$ at a PAR wavelength of the algal culture can be no higher than about 65%, and preferably no higher than about 60%. For example, the depth dimension can be determined by calculating that, for an algal sample reaching an optical density of between about 0.5 and 1.0, between about 1.0 and about 1.5, or between about 1.5 and about 2.0, the absorbance can be less than or equal to about 65%, less than or equal to about 60%, or less than or equal to about 50%, and may be less than or equal to about 45%, or less than or equal to about 40%.

The volume of the growth vessel can be selected to hold a desired sample volume of algae-containing water or growth media. One factor in selecting a desired volume of algae-containing water can be the amount of algae that is needed for performing a desired characterization on the algae. For example, an optical density of about 0.1 will correspond to an algae density of about 0.03 g/L to about 0.05 g/L for some types of algae. One way of characterizing the growth rate of algae can be to measure the ash free dry weight of the algae. For this type of measurement to be repeatable, an average sample should contain at least a few milligrams of algae, such as at least about 0.01 g of algae. Thus, for measuring algae growth for an optical density of about 0.1, it is generally beneficial to have an algae sample volume (and therefore a corresponding growth vessel volume) of at least about a liter.

Alternatively, in some methods provided herein, the algae in the test vessel can be grown to a higher density, for example to an optical density (e.g., at ~730 nm) of 0.5 or greater, for example 1.0 or greater or 1.5 or greater. In these methods, significantly smaller algal test culture volumes can be used, such as, for example, volumes of 500 mL or less, 250 mL or less, 100 mL or less, or 50 mL or less.

Based on a desired vessel depth and a desired volume, a suitable cross-sectional area for the vessel can be selected. For convenience, the growth vessel can have a rectangular type cross-section, with the length and width selected to provide a desired volume. For a vessel depth of about 1 cm and a volume of about 1 liter, this corresponds to a square vessel with approximate dimensions of 31.6 cm×31.6 cm×1 cm. This also corresponds to a rectangular vessel with approximate dimensions of 20 cm×50 cm×1 cm. Additionally, where the vessel depth exceeds 2 cm, and the culture density times the culture depth exceeds 1 cm, the height and width dimensions of the vessel can be considerably smaller, as the culture volume needed for productivity assessment is less. For example, a rectangular vessel having a volume of approximately 150 mL can have approximate dimensions of 8 cm×12.5 cm×2 cm, where 1.9 cm is the oriented as the depth dimension. Alternatively, any other convenient cross-section can be selected, such as a cross-section that facilitates even distribution of light intensity across the surface of the vessel based on the geometry of the illumination source for the growth vessel. Thus, circular, trapezoidal, or other regular or irregular shapes can be selected for the growth vessel.

For ease of use, it may be desirable to have a growth vessel with a volume that is larger than the desired sample volume of algae containing water. For example, a suitable rectangular vessel can have approximate dimensions of 25 cm×50 cm×1.3 cm, which correspond to an internal volume for the growth vessel of ~1.625 liters. During operation, about 1.4 liters of algae-containing water or growth media can be used. In this embodiment, the depth or gauge dimension of the vessel corresponds to the 1.3 cm. The vessel can be oriented so that either the 25 cm or the 50 cm dimension is oriented approximately in the direction of gravitational pull. This can result in the depth dimension being oriented roughly perpendicular to the direction of gravitational pull. The light source for the growth vessel can be located and oriented so that the incident light passes through a surface of the growth vessel having the 25 cm×50 cm cross-sectional area. In this type of configuration, placing about 1.4 liters in a ~1.625 liter vessel will result in an unoccupied volume in the vessel. This unoccupied volume does not change the definition for what is considered the depth dimension. As defined above, the depth dimension corresponds to the dimension roughly perpendicular to the surface that receives the majority of incident light intensity. Those of skill in the art will clearly recognize that the depth or gauge dimension in this embodiment corresponds to the 1.3 cm dimension.

In additional examples, for example, for use in methods where algae are allowed to grow to densities of 0.5 or greater, smaller volume vessels may be used, for example, where the depth dimension may be 2.0 cm or less, and the vessels may hold up to 500 mL, for example, up to 400 mL, up to 300 mL, up to 200 ml, up to 100 mL, up to 50 mL, up to 40 mL, or less than 40 mL, of algal culture. For example, standard disposable essentially-rectangular tissue culture flasks may be used, and can have dimensions of approximately 12.6 cm×7.8 cm×1.9 cm and an internal volume of approximately 150 mL. The flasks may contain, for example, approximately 100 mL of algal culture during the culturing period.

To allow in light, the vessel should be constructed of a material that is transparent or substantially transparent to the incident light used for illuminating algae in the vessel. Suitable materials for the container can include various types of clear glass or plastic. Clear polycarbonate plastic is one useful structural material, as polycarbonate facilitates sterilization of the growth vessel prior to the beginning of a test. It is noted that ultraviolet light is typically not involved in photosynthesis reactions, so UV attenuation due to the structural materials can be acceptable. As an alternative, any attenuation of light by the structural material for the growth vessel can be accounted for by using a correspondingly stronger illumination source, so that the light intensity incident on the surface of the algae-containing water can approximately match the desired model intensity from an illumination profile.

The growth vessel can include other features to allow for control of the reaction conditions in the vessel. For example, the temperature in the growth vessel can typically also be controlled, as algae growth rates are often strongly influenced by temperature. If a relatively stable temperature is desired for the growth vessel, the growth vessel can be placed in a sand bath, with the back side of the vessel in contact with the sand. Another method for controlling the temperature in the growth vessel can be to use one or more thermoelectric heaters. The thermoelectric heaters can be attached to and/or incorporated into a sidewall of the growth vessel. Optionally, the thermoelectric heaters can be located on a sidewall so that the heaters are not in the path for light incident on the algae. When the target temperature for the vessel is higher than the current temperature, the thermoelectric heaters can be used to increase the temperature. When the target temperature is lower than the current temperature, the heaters can be turned off to allow the vessel to cool in a passive manner.

Heating and cooling of the growth vessel can be used to represent the heating and cooling a pond would experience due to exposure to external conditions. A raceway pond can have a depth of only a meter or less, and typically only a few tens of centimeters or less, and therefore a raceway pond may have a relatively constant temperature at any given time. However, the temperature of the pond may vary during the course of a trajectory. For example, during daylight hours a pond can increase in temperature based on incident radiation. Any sunlight that is incident on the pond surface can be assumed to be reflected at the surface, used for algae photosynthesis, or absorbed by the pond and converted to heat. Optionally, the contribution of sunlight to algae photosynthesis can be ignored to simplify the calculation. The pond can also lose heat to the environment via convection, radiative transfer, and other mechanisms. This heat exchange can be modeled to provide a temperature profile for the pond that is correlated with the illumination profile. In other words, each time in the trajectory can have both an illumination value and a temperature value. Note that the illumination and temperature values associated with a time in a trajectory may be illumination and temperature values that span a period of time. For example, a temperature value and/or illumination value may be specified for each 1 second period, each 5 second period, each 10 second period, each 1 minute period, and/or any other convenient period of time. When algae in a growth vessel is exposed to illumination based on an illumination profile, the water in the growth vessel can then be heated or cooled accordingly based on the correlated temperature profile.

Another factor that can be controlled in the growth vessel is the pH of the water. In many embodiments, $CO_2$ can be the primary acidic component in the algae-containing water, and therefore the pH can be controlled by controlling the $CO_2$ content. $CO_2$ can be introduced into the growth vessel via an inlet that allows for bubbling $CO_2$ into the vessel. Alternatively, an aeration port can be used to introduce $CO_2$. A flow meter or another convenient device can be used to control the input flow-rate of $CO_2$ into the growth vessel. During exposure of algae to an illumination profile, it may be desirable to hold the $CO_2$ concentration at a relatively constant value. Alternatively, if a pond is being modeled that has one or a few discreet $CO_2$ input sources, the $CO_2$ concentration experienced by the algae may vary as the algae traverses the pond. Thus, it can be desirable to vary the $CO_2$ concentration during the course of an illumination profile.

Still another factor that can be controlled in the growth vessel is the oxygen content. Algae can produce molecular oxygen as a by-product of photosynthesis. An inlet can be included in the growth vessel to allow for addition of oxygen in order to match a model oxygen content. An aeration port can also be included to allow for removal of oxygen in order to match a model oxygen content.

In addition to inputs to the growth vessel, the growth vessel can also include features to allow for movement of water or growth media within the growth vessel. In examples where the sample volume is small, for example, about 1 liter or less, bubbling of air or $CO_2$ through the culture, for example, by insertion of a tube into the culture, can provide adequate culture mixing. An alternative or additional option can be to include a mechanical agitator in the growth vessel, to increase mixing within the vessel. One or more internal dividers can be included in the growth vessel, such as dividers that can be used to set up a flow path within the vessel. A mechanical paddle wheel or another mechanism can then be used to create a flow within the growth vessel. In further embodiments, a sparging mechanism can be used to provide movement or agitation of the water/growth medium in the growth vessel. As an example, a sparging mechanism could be used for introduction of $CO_2$ into the growth vessel.

In other embodiments, different types of growth vessel may be suitable. For example, another type of screening test can be a test of lipid production. It is noted that the algae may undergo little or no growth during a lipid production test. During a lipid production test, a simplified vessel with a smaller volume may be suitable. The vessel may not need to include inlets or aeration for providing or removing gases during a test run. Instead, the vessel can allow for introduction of an algae sample with a desired initial pH and $O_2$ content. The vessel can then be closed during performance of the test. The temperature can be controlled by any convenient method, such as by using a sand bath or thermoelectric heating. The vessel can then be exposed to an illumination profile for lipid production.

Testing Apparatus—Illumination Source

After generating an illumination profile, an algae sample in the growth vessel can be exposed to the illumination profile by controlling the output of an illumination source. In various embodiments, the illumination source can be capable of delivering light intensity to the surface of the water sample in the growth vessel. The intensity can range from no illumination to an intensity that is at least about the maximum intensity in the illumination profile. The illumination source can be controlled to vary the delivered intensity in accordance with the illumination profile.

One consideration in selecting an illumination source can be the maximum light intensity that is required within an illumination profile. For example, an illumination profile based on sunlight incident on a pond can have a maximum incident intensity corresponding to a maximum incident sunlight intensity. Depending on the modeled location for the pond, this can be up to about 2400 $\mu E/m^2/s$ PAR. Preferably, the illumination source can deliver at least this intensity to the surface of the sample in the growth vessel. Of course, an illumination source capable of delivering a greater intensity can be used, and then scaled back to match the intensity specified in the illumination profile. Alternatively, most known types of algae have a saturation intensity of about 1000 $\mu E/m^2/s$ PAR or less. Thus, in most situations, a light source having an intensity of at least 1000 $\mu E/m^2/s$ PAR is sufficient, such as about 1100 $\mu E/m^2/s$ PAR. For example, consider a rectangular vessel having a cross-sectional area of 20 cm×50 cm. This corresponds to 0.1 $m^2$ of surface area for the algae-containing water in the growth vessel. In order to deliver about 1000 $\mu E/m^2/s$ PAR to this surface area, an illumination source can be used that can deliver at least about 100 $\mu E/m^2/s$ PAR. In various embodiments, the illumination source can deliver to the surface of the vessel at least about 40 $\mu E/m^2/s$ PAR, for example, at least about 80 $\mu E/m^2/s$ PAR, at least about 100 $\mu E/m^2/s$ PAR, or at least about 150 $\mu E/m^2/s$ PAR. Additionally or alternately, the illumination source can deliver to the surface of the vessel about 240 $\mu E/m^2/s$ PAR or less, for example, about 200 $\mu E/m^2/s$ PAR or less, about 150 $\mu E/m^2/s$ PAR or less, or about 120 $\mu E/m^2/s$ PAR or less.

One option for the illumination source can be to use a plurality of light emitting diodes (LEDs). LEDs typically generate non-collimated light, so the LEDs can be used in conjunction with lenses in order to direct the light toward the surface of the water. One feature of some LED light sources is that an LED can have a defined relationship between input power and output illumination over a range of LED outputs. This can allow an LED to deliver a percentage of the input power as output illumination. In the example described above, if an LED has 40% efficiency, a sufficient number of LEDs can be used so that the input power to the LEDs can be about 35-40 W, so that the output power can be at least about 14 W. This can correspond to a light intensity for the LEDs of about 125-150 $\mu E/m^2/s$ PAR (depending on the nature of the LED). The input power to the LED can be regulated by controlling the current delivered to the LED, such as by using a commercially available constant current controller. Because LEDs respond quickly to changes in current, it can often be desirable to use a constant current controller to vary LED output in accordance with an illumination profile.

In an embodiment, an array of LEDs is used that are arranged roughly in the same geometry as the cross-section of the growth vessel, such as a rectangular array for a rectangular growth vessel cross-section. A square shaped pattern lens can be used in front of each LED to approximately direct the light onto the surface of the water in the growth vessel. The LEDs in the array can be selected to have roughly the same light output, and the LEDs can be spaced in a regular pattern to generate a roughly uniform illumination of the water surface in the growth vessel. In other embodiments, other choices for number, type, and spacing of LEDs can be used to generate a desired illumination pattern on the surface of water in a growth vessel.

The algal growth simulation system in many examples will be used to replication growth conditions of a pond or a photobioreactor exposed to sunlight. In replicating these reference embodiments, the light source can be arranged such that the growth vessel is illuminated from a single direction. Thus a typical design that employs a light source such as an array of LEDs can have the LED array positioned on a single side of the growth vessels, i.e., facing the cross-sectional area of the growth vessel referred to above, where light is directed through the depth of the culture.

In some embodiments, the color of the LEDs can be selected to approximate the color spectrum of the light incident on the body of water being modeled. If the modeled light source is sunlight, a white LED can be selected. The output of a white LED will likely have a different mixture of wavelengths than sunlight, but it is not believed to be necessary to exactly match the light source being modeled. In alternative embodiments, an LED with a more limited color spectrum can be used, such as a red or a blue LED.

Because of the intensity requirements, it can be beneficial to use an LED that can convert input energy to light, with relatively high efficiency. This is not essential, but it can help with assembling a sufficient number of LEDs to provide the desired incident intensity in a reasonable amount of area. Examples of suitable LEDs are available from Phillips Lumileds Lighting Co. and Cree, Inc.

In order to deliver a desired amount of illumination to an algae sample, the illumination delivered at various power levels by a light source array (such as an LED array) can be measured. This can allow for calibration of the light source array in advance. Alternatively, if an existing relationship is known between input power and output illumination, the light source array can be used based on the expected relationship.

Operating Conditions—Algae Growth

Based on an illumination profile and one or more corresponding condition profiles, algae growth in a larger scale body of water can be simulated using a smaller scale reactor or culture vessel. First, a body of water to be simulated can be selected, such as a pond or a photobioreactor. As described above, a computational fluid dynamics program can be used to generate representative trajectories for algae traveling through the body of water, or fluid flow field can be developed based on measurements of an existing body of water. The trajectories can be used to determine an illumination profile. Additionally, a corresponding temperature profile can be determined. If desired, a corresponding pH profile, $O_2$ profile, and/or a profile for other controlled variables can be developed.

Using the illumination profile, algae can be grown in a growth vessel. In some methods, a desired concentration of algae can be introduced into the growth vessel. The concentration of algae can be selected based on a desired optical density for the algae and water in the growth vessel. The desired optical density can be at least about 0.01, for example at least about 0.05, at least about 0.1, or at least about 0.2. The desired optical density can additionally or alternatively be about 0.6 or less, for example about 0.5 or less, about 0.3 or less, about 0.2 or less, or about 0.1 or less. Although an optical density of about 0.5 can lead to some light attenuation even in a vessel with a depth of 1 cm, it is believed that results generated at this type of optical density can still be representative of a reference system.

In some embodiments, the depth of the growth vessel can be selected based on a desired optical density for simulation. For example, if it is desired to measure algae growth at an optical density of about 0.1, a vessel having dimensions of about 20 cm×50 cm×1 cm may be suitable. If it is desired to measure algae growth at an optical density of 0.5, a similar vessel could be used, or a vessel having dimensions of 40 cm×50 cm×0.5 cm may be suitable. Similarly, if a more dilute solution of algae is desirable, a vessel with a greater depth than 1 cm may be appropriate.

Algae in the vessel can then be exposed to an illumination profile for a period of time, referred to herein as the sample culturing period, such as an hour, multiple hours, a day, multiple days, or even months. As the algae grow, the concentration of algae in the growth vessel can increase, which can lead to an increase in optical density. For testing of growth at a given optical density, the sample in the vessel can be diluted on a periodic basis to return the growth vessel to the original optical density. For example, on a daily basis water in the vessel can be sampled and the optical density can be measured, such as in a spectrophotometer. Based on the measured optical density, the algae in the vessel can be diluted to return the optical density to the desired optical density. The water can be sampled again to verify that the desired optical density has been achieved. This technique can allow for simulation of a long period of growth while maintaining an optical density that does not result in excessive attenuation.

In alternative methods, the optical density of a simulator culture may be allowed to increase during the sample culturing period. In these methods, the algae sample may be exposed to an illumination profile without regular dilution of the sample culture during the sample culturing period. This can allow for smaller volume sample cultures, as the biomass of the algae sample increases with the optical density. For example, the optical density of the algal sample can be allowed to reach a value of at least about 0.3, at least about 0.5, at least about 1.0, or greater, such as an optical density of between about 0.5 and about 1.0, between about 1.0 and about 1.5, between about 1.5 and about 2.0, at least about 2.0, between about 2.0 and about 2.5, or greater than about 2.5, during the sample culturing period. For example, the maximal optical density during the culturing period can be about 3.0 or less, for example about 2.5 or less, about 2.0 or less, about 1.5 or less, about 0.8 or less, about 0.6 or less, about 0.5 or less, or about 0.3 or less. Although an optical density of about 0.5 or greater can lead to some light attenuation even in a vessel with a depth of 1 cm, it is demonstrated herein that results generated at optical densities of greater than 0.5 and sample depths of greater than 1.0 cm can still be representative of a modeled system such as a mixed pond or bioreactor.

For example, the simulation can be run where the cultures are allowed to reach an OD of at least about 0.3 or at least about 0.5, such as between about 0.5 and about 1.0, between about 1.0 and about 1.5, between about 1.5 and about 2.0, between about 2.0 and about 2.5, or between about 2.5 and about 3.0, and the growth vessel can be between about 0.5 cm and about 1.0 cm in width, for example between about 1 cm and about 1.5 cm in width, between about 1.5 cm and about 2 cm in width, or between about 2.0 cm and about 2.5 cm in width. The other dimensions of the vessel may be reduced accordingly to provide a convenient volume of culture having a biomass of at least about 10 mg at the end of the simulator run.

In such examples, the sample cultures can have a volume of, for example, less than about one liter, less than about 500 mL, less than about 200 mL, less than or equal to about 100 mL, or less than or equal to about 50 mL. In these methods, a simulator culture can preferably be monitored regularly, such as daily, for optical density, and the optical density of the simulator culture can be programmed into the simulator system to modify the illumination profile, taking into account the updated (i.e., most recent) sample optical density value which is used in calculating light attenuation. In this way, the simulator culture can provide one or more updated values for optical density that can be used in modeling the light attenuation of an algal reference culture over time, which can be used to provide a modified illumination profile, such as a first modified illumination profile, and the algae sample can then be exposed to the (first) modified illumination profile as the culturing period continues. Further, until a second updated optical density can be measured and a second modified illumination profile can be calculated and applied to the sample culture. The modified light attenuation profile(s) can be based on optical density increases in the sample that may model increases in culture density that occur in a growth environment, such as the modeled reference growth environment.

For example, in these methods, the algae can be allowed to grow without dilution for two, three, four, five, six, seven or more days, or for the same amount of time as they would be expected to grow in a reference volume (e.g., a mixed pond), where, in some preferred embodiments, the cultures are not diluted during this culture period. Optical density measurements of the sample cultures can be taken daily or at any convenient time interval, and these updated optical density values can be programmed into the simulator system to modify the light intensity profile as the simulation sample culturing period progresses, to more accurately model increased light attenuation based on increased density of an algal culture over time. Thus, in these methods, the algae sample can be exposed to an initial illumination profile that is subsequently modified based on measurements of optical density of the sample cultures, whereupon the algae sample is exposed to a modified illumination profile that takes into account the updated optical density. Illumination profiles may be modified at regular intervals, such as, for example, daily, based on optical density measurements taken at regular intervals, e.g., daily. For example, an algae sample can be exposed to a first illumination profile at a first stage of the sample culturing period, and can subsequently be exposed to a second modified illumination profile during a second stage of the sample culturing period, where the second illumination profile is calculated using a second updated optical density measurement taken during the sample culturing period. The algae sample can be exposed to one, two, three, four, five, six, seven, eight, nine, ten, or more modified illumination profiles during the sample culturing period, where successive modified illumination profiles can be based on successive updated algae sample optical densities measured during the sample culturing period.

In preferred examples, the maximum optical density of the algal sample during the scale-down sample culturing period allows for a culture absorbance $((I_0-I_L/I_0) \times 100\%)$ at a PAR wavelength of at least about 30%, for example, at least about 35%, at least about 40%, or at least about 45%. For instance, the culture absorbance can reach a value of between about 35% and about 40%, between about 40% and about 45%, between about 45% and about 50%, between about 50% and about 55%, or between about 55% and about 60%. The transmittance $(I_L/I_0)$ of the algal sample can preferably be maintained at at least 35%, and more preferably at at least 40%, at least 45%, or at least 50%, during the culture period. Using Beer's Law as provided above, where absorbance=$\alpha L$=$-\log_{10}(I_L/I_0)$=$\epsilon Lc$, it can be seen that the transmittance can be maintained at a level at or above 35% by adjusting the depth of the flask (L) and/or the optical density of the culture.

In instances where an algal sample cultured in a algal growth simulator system reaches a density of greater than about 0.3, such as greater than about 0.4, greater than about 0.5, or at least about 0.6, the culture vessel can have reduced dimensions with respect to the examples above. For example, a culture vessel can be 10 cm or less×25 cm or less×1 cm or 8 cm×15 cm×2 cm, etc. The ability of a culture vessel to simulate growth of algae in the reference volume can be determined empirically, and can be aided by determining or approximating the extinction coefficient profile of the algal strain or a taxonomically related strain.

After a desired amount of exposure of algae to an illumination profile (or a series of illumination profiles, where an initial illumination profile is followed by one or more modified illumination profiles) one or more tests are then performed on the algae to identify samples likely to perform well in the modeled larger scale open, closed, or hybrid bioreactor. One type of test can be a measurement of the ash free dry weight of an algae sample. Measuring the ash free dry weight can provide a value for the growth rate of an algae sample relative to a starting algae concentration. To measure the ash free dry weight, at least a portion of the algae sample in the vessel can be withdrawn. The withdrawn sample can be filtered to separate solid matter from the surrounding water. The sample can then be further dried to remove additional water. The additional drying can include heating of the sample, but combustion of any portion of the sample should be avoided. The dried sample can then be weighed. After determining a pre-combustion weight, the sample can be combusted. The ash remaining after combustion can be dried and then weighed. The difference between the initial weight and the amount of ash (the ash free dry weight) provides a numerical value for the amount of biomaterial in the original sample.

Another type of measurement can be a measurement of the total organic carbon in an algae sample. Many variations for total organic carbon analysis are available. Methods for total organic carbon analysis typically involve an initial acidification of a sample to drive dissolved $CO_2$ out of the sample. The sample can then be combusted or oxidized by various methods, and the $CO_2$ evolved from combustion/oxidation can be measured as an indication of carbon content. The evolved carbon can be measured by measuring a conductivity of the sample before and after evolution of $CO_2$, or by non-dispersive infrared analysis. For example, total organic carbon for an algal sample can be analyzed using a Shimadzu TOC-VCSH Analyzer, which efficiently oxidizes organic compounds.

Still another type of characterization can be lipid productivity. For example, the total amount of lipids present in an algae sample can be measured by fatty acid methyl ester (FAME) analysis, in lipids from algae are determined as fatty acid methyl esters by gas chromatography. Lipid productivity can be useful for measuring the capability of an algae sample for generating the lipid products which can eventually be converted into a diesel fuel or other valuable product. For methylation of free fatty acids and transmethylation of lipids the AOCS method Ce 1j-07 is used with some modifications, followed by alkali hydrolysis and methylation.

To determine the fatty acid ester content by FAME analysis, an algal culture sample (~2 mL) can be lyophilized to dryness followed by alkali hydrolyses with ~700 uL of ~0.5 M KOH in methanol/tetrahydrofuran (~2.5:1) mix. Glass beads can be added to the tubes, which can then be vortexed and then heated at ~80° C. for ~5 mins. The tubes can be allowed to cool ~5 mins at room temperature (~20-25° C.), before methylation with ~500 µL of ~10% $BF_3$ at ~80° C. for ~30 mins. Vials can then be allowed to cool ~5 mins before extraction with ~2 mL of heptane and ~500 uL of ~5 M NaCl. After vortexing, samples can be centrifuged for ~1 min at ~2000 rpm to separate phases. About 0.9 µl of the hexane extract can be injected into an Agilent 7890A gas chromatography system at a flow rate of ~0.5 mL/min hydrogen at ~100° C. for about 1 min, followed by a relatively fast temperature gradient to ~230° C. for ~1.7 mins. A DB-FFAP capillary column (J&W Scientific) can be used, ~10 m long with ~0.10 mm diameter and ~0.10 µm film thickness. The inlet can be held at ~250° C., and the FID detector at ~260° C.

Peaks can be identified based on external standards. Absolute areas for both analytes and the internal standards can be obtained and the amount of FAME calculated for each sample. The efficiency of derivatization of triacylglycerides can be determined by computing the ratio between FAME originating from a triacylglyceride internal standard (e.g., C13:0) and FAME originating from a FAME internal standard (e.g., C23:0). The efficiency of derivatization of fatty acids can be determined by computing the ratio between FAME originating from an internal standard free fatty acid (e.g., C11:0) and FAME originating from an internal standard FAME, (e.g., C23:0) (The ratios should be close to 1.).

To determine the total organic carbon (TOC) content of algal cells, samples of cell cultures can be centrifuged to remove media and resuspended in water. Cell samples (three per measurement) can be injected into a Shimadzy TOC-Vcsj Analyzer for determination of Total Carbon, Total Inorganic Carbon, and, optionally, Total Nitrogen. The combustion furnace can be set to ~720° C., and TOC can be determined by subtracting TIC from TC. The calibration range can be from ~2 ppm to ~200 ppm. The correlation coefficient requirement is preferably $r^2>0.999$.

In addition, scale-down cultures can be tested for photosynthetic properties, including, for example, Fv/Fm, oxygen evolution, and non-photochemical quenching. The scale-down cultures can be used to assay for or perform chemical analysis to detect metabolites, pigments, particular lipids, cofactors, or enzymes. The scale-down cultures can also be tested for expression of particular genes or production of proteins, for example using PGR, nucleic acid hybridization, antibody detection, or other techniques.

The system can include more than one growth vessel, and can test replicate cultures of a strain, optionally can test more than one growth condition for a strain, and/or can test more than one strain of algae during a single run. In some examples, algal mutants and parent wild-type strains can be tested together, where the algal mutants and the parent strain have similar molar absoptivities. The productivities of strains can be assessed and compared with one another based on productivities or growth rates, for example, or biochemical or molecular genetic assays or analysis can be performed on the cells of the simulator cultures. The results of growth, productivity, biochemical, or molecular genetic (e.g., gene expression) analysis can be used to screen and/or compare algal strains and mutants, including genetically engineered strains, in a simulated environment prior to or in lieu of, testing in large volume growth systems.

Alternative Configurations—High Throughput Testing

The above systems and methods provide examples for simulating algae growth and/or lipid production in a larger body of water (such as a photobioreactor or pond) using a small scale system. In other embodiments, algae growth and/ or lipid production can be simulated in multiple vessels in parallel at the same time. If sufficient space is available, multiple vessels of any convenient size, for example, a size of from 100 microliters to 1 liter, or any other convenient size, can be exposed to illumination profiles in parallel. For example, multiwell plates can be used, or can be adapted for use, in which in various nonlimiting embodiments the wells of a 96-well, 48-well, 24-well, 12-well, or 6-well multiwell plate can contain, for example, 100 microliters, 200 microliters, 1 milliliter, 2 milliliters, 3 milliliters, 4 milliliters, or 5 milliliters of water or culture media. Alternatively, multiple smaller vessels can in some embodiments be exposed to illumination to test for features that can be measured with a smaller sample size, such as lipid productivity.

One way to enable high throughput testing can be to have multiple banks of LEDs that can be controlled separately as an illumination source. Using lenses, the light from each bank of LEDs can be approximately focused to impinge on one or more selected growth vessels. For example, consider an illumination device with four banks of LEDs. The banks can be arranged in rows. Each row can be used to provide a different illumination profile. One or more growth vessels can be positioned to receive illumination from each of the banks. One option could be to have a plurality of growth vessels arranged in columns, with the same type of algae in each vessel in a column. In this manner, a matrix of algae growth and/or lipid production experiments can be ran at the same time, as each vessel will represent a unique combination of an algae (arranged by column) and illumination profile (arranged by row). Of course, other ways of arranging light banks and growth vessels will be apparent to those of skill in the art.

Types of Algae

An algal strain can include any isolate of an algal species or subspecies, and includes mutants and genetically engineered strains. Algae considered herein can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/ or Haptophyta, Bacillariophyceae, Eustigmatophyceae, Trebouxiophyeeae, or Prasinophyceae. Specific species can include, but are not limited to, *Neochloris oleoabundans,*

*Scenedesmus dimorphus, Euglena gracilis, Phaeodactylum tricornutum, Pleurochrysis carterae, Prymnesium parvum, Tetraselmis chui, Nannochloropsis gaditana, Dunaliella salina, Dunaliella lertiolecta, Chlorella vulgaris, Chlorella variabilis,* and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carieria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeieria, Hymenomonas, Isochrysis, Lepocinclis, Micraciinium, Monoraphidium, Nannochloris, Nannochloropsis, Navicula, Neochloris, Nephrochloris, Nephroselmis, Nitzschia, Ochromonas, Oedogonium, Oocystis, Oslreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella,* or *Volvox* species, and/or one or more cyanobacteria of the *Agmenellum, Anahaena, Anabaenopsis, Anacystis, Aphanizomenon, Arlhrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cyiindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, lyengariella, Leptolyngbya, Limnothrix, Lyngbya, Microcoleus, Microcystis, Myxosarcina, Nodularia, Nostoc, Nostochopsis, Oscillaioria, Phormidium, Planktothrix, Pleurocapsa, Prochlorococcus, Prochloron, Prochlorothrix, Pseudanabaena, Rivularia, Schizothrix, Scytonema, Spirulina, Sianieria, Starria, Stigonema, Symploca, Synechococcus, Synechocystis, Tolypothrix, Trichodesmium, Tychonema,* and *Xenococcus* species.

Algae oils or lipids are typically contained in algae in the form of membrane components, storage products, and metabolites. Certain algal strains, particularly microalgae such as diatoms, certain chlorophyte species, and cyanobacteria, contain proportionally high levels of lipids. Algal sources for the algae oils can contain varying amounts, e.g., from 2 wt % to 40 wt % of lipids, based on total weight of the biomass itself. The scale-down systems and methods described herein can be used to evaluate production of lipids by algae strains.

Other Embodiments

Additionally or alternatively to any of the described methods and systems, the present invention can include one or more of the following embodiments:

Embodiment 1

A method for prediction of algal behavior in a reference environment based on growth of algae of an algal strain in a controlled environment for a period of time corresponding to the culture period, comprising: calculating a particle trajectory for a particle in a reference volume, the particle trajectory comprising at least a plurality of position values in the reference volume, the plurality of position values having associated times, the position values including at least a depth value relative to a surface of the reference volume; determining an illumination profile based on the particle trajectory by obtaining an illumination intensity corresponding to the plurality of position values and associated times, wherein determining an illumination profile comprises: selecting a depth value and an associated time; selecting an intensity of illumination that is incident on a surface of the reference volume at the associated time; selecting an optical density at the associated time; and calculating an illumination for the selected depth value based on an attenuation of the selected incident illumination intensity and the selected optical density; exposing an algae sample in a vessel to light intensity corresponding to the illumination profile, the algae sample having a sample depth, a sample volume, and an optical density, a product of the optical density and the sample depth being less than about 4.0 cm, the sample volume being less than the reference volume; and characterizing at least one algae property for algae in the reference volume based on at least one measured algae property of the algae sample.

Embodiment 2

A method for prediction of algal behavior in a reference environment based on growth of algae in a controlled environment, comprising: (i) calculating a particle trajectory for a particle in a reference volume, the particle trajectory comprising at least a plurality of position values in the reference volume, the plurality of position values having associated times, the position values including at least a depth value relative to a surface of the reference volume; (ii) determining an initial illumination profile based on the particle trajectory by obtaining an illumination intensity corresponding to the plurality of position values and associated times, wherein obtaining an illumination intensity corresponding to the plurality of position values and associated times comprises: selecting a depth value and an associated time; selecting an intensity of illumination that is incident on a surface of the reference volume at the associated time; selecting an optical density at the associated time; and calculating an illumination for the selected depth value based on an attenuation of the selected incident illumination intensity and the selected optical density; (iii) exposing an algae sample in a vessel to light intensity corresponding to the initial illumination profile, the algae sample having a sample depth, a sample volume less than that of the reference volume, and an optical density, wherein the optical density varies over the sample culturing period; (iv) measuring the optical density of the algae culture during the sample culturing period to obtain an updated sample optical density; (v) modifying the illumination profile in (ii) by selecting the updated sample optical density as the optical density at the associated time to calculate an illumination for the selected depth value based on an attenuation of the selected incident illumination intensity and the updated sample optical density; (vi) exposing the algae sample to light intensity corresponding to the modified illumination profile; and characterizing at least one algae property for algae in the reference volume based on at least one measured algae property of the algae sample.

Embodiment 3

The method of embodiment 2, wherein steps (iv) and (v) are performed at least twice, preferably at regular intervals, for example, twice a day, daily, or every other day, and/or wherein the culture is not diluted during the culturing period.

Embodiment 4

The method of any one of embodiments 1-3, wherein any or any combination of the following hold: the light intensity is directed toward the algae sample from a single side of the vessel, the product of the optical density and the sample depth is less than about 8.0 cm, less than about 6.0 cm, less than about 4.0 cm, less than about 3.0 cm, less than about 2.0 cm, or less than about 1 cm and/or culture absorbance is at least 30%, at least 45%, or at least 50%, during the culture period.

Embodiment 5

A method for comparing algae samples, comprising: (i) calculating a particle trajectory for a particle in a reference volume, the particle trajectory comprising at least a plurality of position values in the reference volume, the plurality of position values having associated times, the position values including at least a depth value relative to a surface of the reference volume; (ii) determining an illumination profile based on the particle trajectory by obtaining an illumination intensity corresponding to the plurality of position values and associated times; (iii) exposing a first algae sample in a first vessel to light intensity corresponding to the illumination profile, the first algae sample having a first sample depth, a first sample volume, and a first optical density, a product of the first optical density and the first sample depth being less than about 10.0 cm, the first sample volume being less than the reference volume; (iv) exposing a second algae sample in a second vessel to light intensity corresponding to the illumination profile, the second algae sample having a second sample depth, a second sample volume, and a second optical density, a product of the second optical density and the second sample depth being less than about 10.0 cm, the second sample volume being less than the reference volume, at least one environmental factor of the second vessel being different from a corresponding at least one environmental factor of the first vessel; (v) characterizing at least one algae property for the first algae sample; characterizing the at least one algae property for the second algae sample; and (vi) comparing the characterized at least one algae property for the first algae sample and the characterized at least one algae property for the second algae sample to determine the comparative effect of the at least one environmental factor.

Embodiment 6

The method of embodiment 5, wherein the at least one environmental factor that is different for the first algae sample and the second algae sample is a speed of mixing, a presence of a mixing structure, a presence of mixing jets, a $CO_2$ concentration, an $O_2$ concentration, a pH, the presence or concentration of a nutrient, an algae sample depth, a temperature, or a combination thereof.

Embodiment 7

A method for comparing algae samples, comprising: (i) calculating a particle trajectory for a particle in a reference volume, the particle trajectory comprising at least a plurality of position values in the reference volume, the plurality of position values having associated times, the position values including at least a depth value relative to a surface of the reference volume; (ii) determining an illumination profile based on the particle trajectory by obtaining an illumination intensity corresponding to the plurality of position values and associated times; (iii) exposing a first algae sample comprising a first algal strain in a first vessel to light intensity corresponding to the illumination profile, the first algae sample having a first sample depth, a first sample volume, and a first optical density, a product of the first optical density and the first sample depth being less than about 10.0 cm, the first sample volume being less than the reference volume; (iv) exposing a second algae sample comprising a second algal strain in a second vessel to light intensity corresponding to the illumination profile, the second algae sample having a second sample depth, a second sample volume, and a second optical density, a product of the second optical density and the second sample depth being less than about 10.0 cm, the second sample volume being less than the reference volume; (v) characterizing at least one algae property for the first algae sample; characterizing the at least one algae property for the second algae sample; and (vi) comparing the characterized at least one algae property for the first algae sample and the characterized at least one algae property for the second algae sample to determine the difference in at least one algal property between the first algal strain and the second algal strain.

Embodiment 8

The method of any one of embodiments 6-8, wherein the first vessel and the second vessel are the same, the method further comprising: removing the first algae sample from the vessel after the exposure of the first algae sample to the illumination profile; and introducing the second algae sample into the vessel.

Embodiment 9

The method of any one of embodiments 5-8, wherein comparing the characterized at least one algae property for the first algae sample and the characterized at least one algae property for the second algae sample comprises: measuring one or more algae properties for the first algae sample; measuring the one or more algae properties for the second algae sample; characterizing the at least one algae property for the first algae sample based on the measured one or more algae properties for the first algae sample; and characterizing the at least one algae property for the second algae sample based on the measured one or more algae properties for the second algae sample.

Embodiment 10

The method of any one of the previous embodiments, wherein calculating a particle trajectory comprises: measuring a velocity field for a fluid flow in the reference volume; and constructing a particle trajectory in the fluid flow using a stochastic process or modeling a fluid flow in the reference volume; simulating a plurality of particle traces in the modeled fluid flow in the reference volume; and constructing a particle trajectory based on a combination of one or more particle traces from the plurality of particle traces, wherein the particle trajectory is optionally constructed from one or more randomly selected particle traces.

Embodiment 11

The method of any one of the previous embodiments, wherein the particle trajectory comprises a continuous function of locations within the reference volume, the location function being a function of time and/or the plurality of position values further comprises a plurality of lateral location values within the reference volume.

Embodiment 12

The method of any one of the previous embodiments, wherein determining an illumination profile comprises:

selecting a depth value and an associated time; selecting an intensity of illumination that is incident on a surface of the reference volume at the associated time; selecting an optical density at the associated time; and calculating an illumination for the selected depth value based on an attenuation of the selected incident illumination intensity and the selected optical density, preferably wherein the optical density α is defined by the equation $\alpha L = -\log_{10} (I_L/I_0)$, where $I_0$ represents an intensity of light incident at a surface and $I_L$ represents an intensity of light at distance L from the surface.

Embodiment 13

The method of any one of the previous embodiments, further comprising determining a temperature profile at the associated times, the temperature profile being associated with at least one of the reference volume and the position values.

Embodiment 14

The method of any one of the previous embodiments, wherein characterizing at least one algae property for algae in the reference volume comprises: withdrawing at least a portion of the algae sample and measuring a property of the withdrawn algae sample portion, optionally wherein the property is compared on a per OD, per ash free dry weight, per total organic carbon, per chlorophyll basis, or wherein the measuring the property of the withdrawn sample portion includes: calculating an algae growth rate; selecting an initial algae concentration for the reference volume; and characterizing the at least one algae property in the reference volume based on a relationship between the initial algae concentration for the reference volume, an algae concentration for the vessel or the withdrawn algae sample, and the calculated algae growth rate, optionally wherein selecting an initial algae concentration for the reference volume comprises determining an initial algae concentration based on a selected optical density for the reference volume.

Embodiment 15

The method of any one of the previous embodiments, wherein the sample volume of the algae sample, the first algae sample, or the second algae sample is less than about 50% of the reference volume, less than about 25% of the reference volume, preferably less than about 5% of the reference volume, and more preferably, less than about 1% of the reference volume.

Embodiment 16

The method of any one of the previous embodiments, wherein the at least one characterized algae property is biomass accumulation, ash free dry weight, total organic carbon, lipid accumulation, expression of one or more genes, activity of one or more enzymes, accumulation of one or more proteins, concentration of one ore more metabolites, growth rate, chlorophyll content, carotenoid content, oxygen evolution, non-photochemical quenching, or $F_v/F_m$.

Embodiment 17

The method of any one of the previous embodiments, wherein the sample volume of the algae sample, the first algae sample, or the second algae sample is less than about 5 L, e.g., less than about 2 L, less than about 1 L, less than about 500 ml, less than about 200 ml, or less than or equal to about 100 ml.

Embodiment 18

A system for exposing algae samples to illumination, comprising: a vessel having a depth of about 10 cm or less and a cross-sectional area, the depth and the cross-sectional area corresponding to a vessel volume of less than about 5 liters; a plurality of light sources positioned so that emitted light is incident on a vessel surface having an area corresponding to the cross-sectional area; a plurality of lenses positioned to increase a percentage of emitted light that is incident on the vessel surface; a memory for storing at least a portion of an illumination profile; and a processor capable of controlling at least one power source for the plurality of light sources based on the stored at least a portion of an illumination profile, wherein the plurality of light sources and the plurality of lenses are positioned to be capable of delivering at least about 1000 $\mu E/m^2/s$ PAR of illumination to the vessel surface, optionally wherein the plurality of light sources comprise at least one light emitting diode, and wherein the at least one power source optionally comprises a constant current controller.

Embodiment 19

The system of embodiment 18, further comprising: a thermoelectric heater in contact with a surface of the vessel; a memory for storing at least a portion of a temperature profile; and a processor capable of controlling the thermoelectric heater based on the stored at least a portion of an temperature profile.

Embodiment 20

The system of any one of embodiments 18-19, the vessel further comprising one or more of a thermometer, a thermocouple, a pH probe, and an aeration port and optionally further comprising a manual or automated agitator.

EXAMPLES

Example 1

Simulation of Raceway Greenhouse Pond

The following example shows the capability for systems and methods according to the invention to simulate algae growth in a larger body of water. In this example, the larger body of water being simulated was a raceway pond contained within a greenhouse. The illumination source for the raceway greenhouse pond was sunlight. The growth vessel for simulating the pond was an about 1.6 liter vessel with interior volume dimensions of about 25 cm×50 cm×1.3 cm. The simulation growth vessel was illuminated by a plurality of LEDs with square lenses, with a maximum incident light intensity of about 1100 $\mu E/m^2/s$ PAR. The same strain of algae was introduced into both the raceway greenhouse pond and the simulation growth vessel.

As a preliminary step, velocimetry measurements were made on the pond system to determine a flow pattern within the pond. The measured flow pattern was then used in a stochastic algorithm to provide for calculation of the depth of an algae sample as a function of time. This is believed to be equivalent to generating a computational fluid dynamics trajectory for algae within a modeled system. Additionally, at periodic times during the experiments, the optical density and the specific absorption coefficient for the raceway greenhouse pond were measured. These periodic measurements were used in conjunction with the real time data mentioned below to control the illumination source for the simulation growth vessel.

In this example, the illumination profile and temperature profile for simulating algal growth were measured from the pond. A temperature sensor in the pond (sampling rate of 1 kHz) was used to control a thermoelectric heater on the growth vessel. The illumination source for the growth vessel was also controlled based on measured values from the pond. Incident light at the surface of the pond was measured (sampling rate of 10 Hz). Using the stochastic algorithm, the depth was also recalculated with a frequency of 10 Hz. Based on the optical density and/or the absorption coefficient for the pond, the incident light and selected height were used to calculate an amount of illumination reaching the model algae cells. Based on the calculated value, the amount of power delivered to the LEDs (illumination source) was varied. Thus, both the temperature profile and the illumination profile provided to the growth vessel were based on the measured values for the raceway greenhouse pond. In the simulated growth vessel, the sample was periodically diluted to maintain an optical density between 0.1 and 0.15. The temperature and illumination data from the pond were used as profiles for the simulated growth vessel for a 4 day period.

FIG. 1 shows a comparison of the temperature measured in the pond versus the temperature measured in the simulated growth vessel during a portion of the experiment. As shown in FIG. 1, the temperature in the simulated growth vessel tracked the temperature from the pond to within about +/−1° C. Thus, the temperature conditions in the pond and the simulated growth vessel were comparable over the 4 day period shown in FIG. 1.

Figure 2:
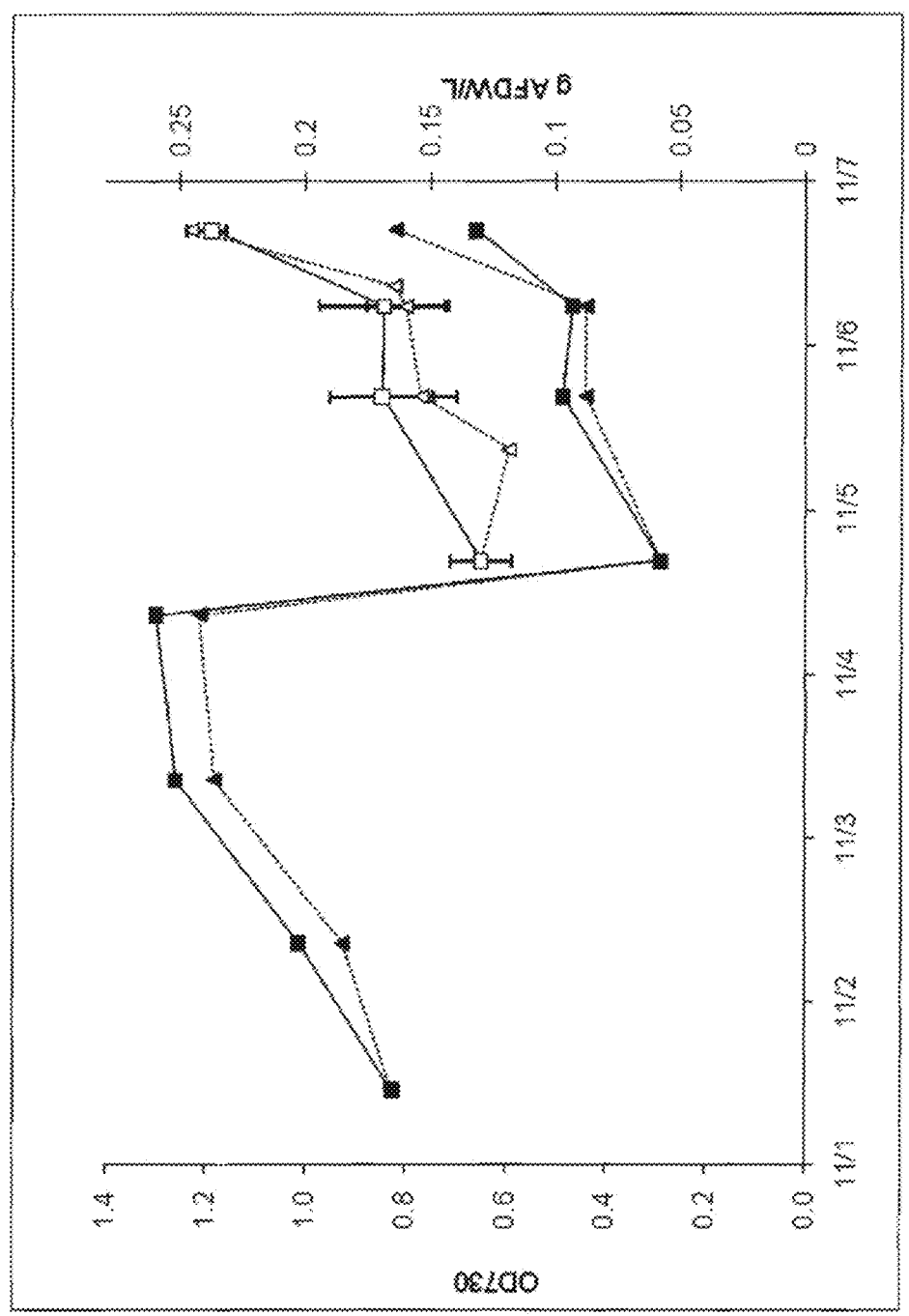

FIG. 2 shows a comparison of optical density (OD) and ash free dry weight (AFDW) values generated from the pond and the simulated growth vessel during the course of the experiment. The optical density values correspond to filled symbols, while ash free dry weight values correspond to open symbols. The triangle symbols correspond to data measured from the pond, while the squares correspond to data based on the simulated growth vessel. In FIG. 2, optical density values for the pond were measured from the beginning of experiment. In the simulated growth vessel, the optical density was not allowed to reach the values near to or greater than 1 shown in FIG. 2. The optical density was reset each day to a value between 0.1 and 0.15 by diluting the contents of the simulated growth vessel. Instead, the optical density values shown in FIG. 2 for the simulated growth vessel represent an optical density calculated based on the growth rates observed for the algae in the simulated growth vessel. In other words, an initial concentration of algae in the pond was known on day 1, along with a corresponding optical density. These values provided a correlation between algae concentration and optical density. For the simulated growth vessel, the algae concentration was initially selected to provide an optical density of about 0.1. After the first day, the optical density in the growth vessel was measured. This provided a growth rate for the algae. This growth rate was used, in combination with the initial algae concentration for the pond, to generate an expected pond algae concentration and corresponding optical density. These expected pond optical densities based on the measured growth rates in the simulated growth vessel are shown in FIG. 2. As shown in FIG. 2, the optical density predicted by the simulated growth vessel tracks the measured value from the pond to within about 10-15%. Thus, even though the simulated growth vessel operates at lower concentrations, the simulated growth vessel was able to approximately reproduce the growth rate in the pond. It is noted in FIG. 2 that the pond was diluted on day 4 of the experiment. At the dilution event, the new measured optical density for the pond was used as a new baseline value for predictions of optical density based on measured growth in the simulated growth vessel.

FIG. 2 also shows ash free dry weight values (the open symbols) for algae from the pond and algae from the simulated growth vessel. As shown in FIG. 2, the ash free dry weight values from the simulated growth vessel also track the pond values to within about 10%. As for the optical density, the ash free dry weight values for the simulated growth vessel represent calculations based on measured values. Due to the lower concentration (and corresponding lower optical density) in the simulated growth vessel, the ash free dry weight values from the growth vessel were used to determine a growth rate for the algae. This growth rate was then used in conjunction with the starting concentration in the pond after the pond dilution event on day 4 to generate the ash free dry weight values shown in FIG. 2.

Figure 3:
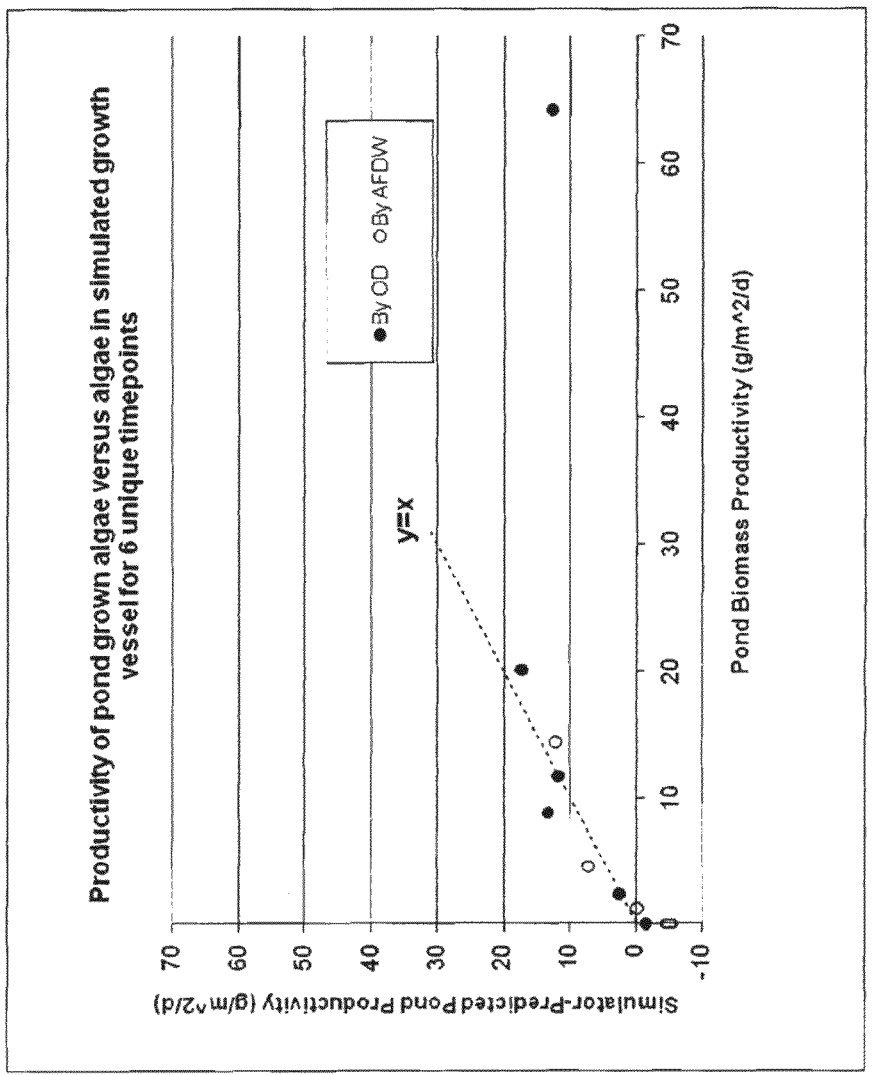

FIG. 3 provides a different type of plot for viewing the data shown in FIG. 2. In FIG. 3, the optical density (OD) and the ash free dry weight (AFDW) calculated based on the simulated growth vessel results are plotted relative to the measured values from the pond. In a plot of the style shown in FIG. 3, if the simulated growth vessel calculated results were identical to the results measured from the pond, all of the data points would reside on the x=y line shown in FIG. 3. Thus, FIG. 3 provides another way of showing the differences between the measured values from the pond, and the calculated values based on the measurements in the simulated growth vessel. As shown in FIG. 3, only one optical density data point generated from the simulated growth vessel did not correspond to the measured pond value to within about 10-15%. Otherwise, the values generated based on the simulated growth vessel tracked the values measured from the pond.

Example 2

Comparison of Algae Grown Using Various Illumination Profiles

In various embodiments, systems and methods according to the invention can allow for growth of algae in a small scale reactor while reproducing growth rates that correspond to growth in a larger scale system. In addition to approximately reproducing the quantitative growth rates, the inventive methods can also provide a benefit in producing algae that qualitatively behave similar to algae grown in a larger scale system. One physiological parameter that can vary greatly depending on how a culture is grown is the culture's potential to utilize non-photochemical quenching processes. Non-photochemical quenching (NPQ) is a protective mechanism utilized by algae to prevent damage induced by excessive light. However, NPQ can be wasteful, and therefore high non-photochemical quenching activity can represent a negative trait for an algae sample. By exposing algae to an illumination profile comparable to the illumination in a larger scale reference geometry, algae produced according to the invention provide a better reproduction of non-photochemical quenching behavior in the larger scale environment.

Figure 4:
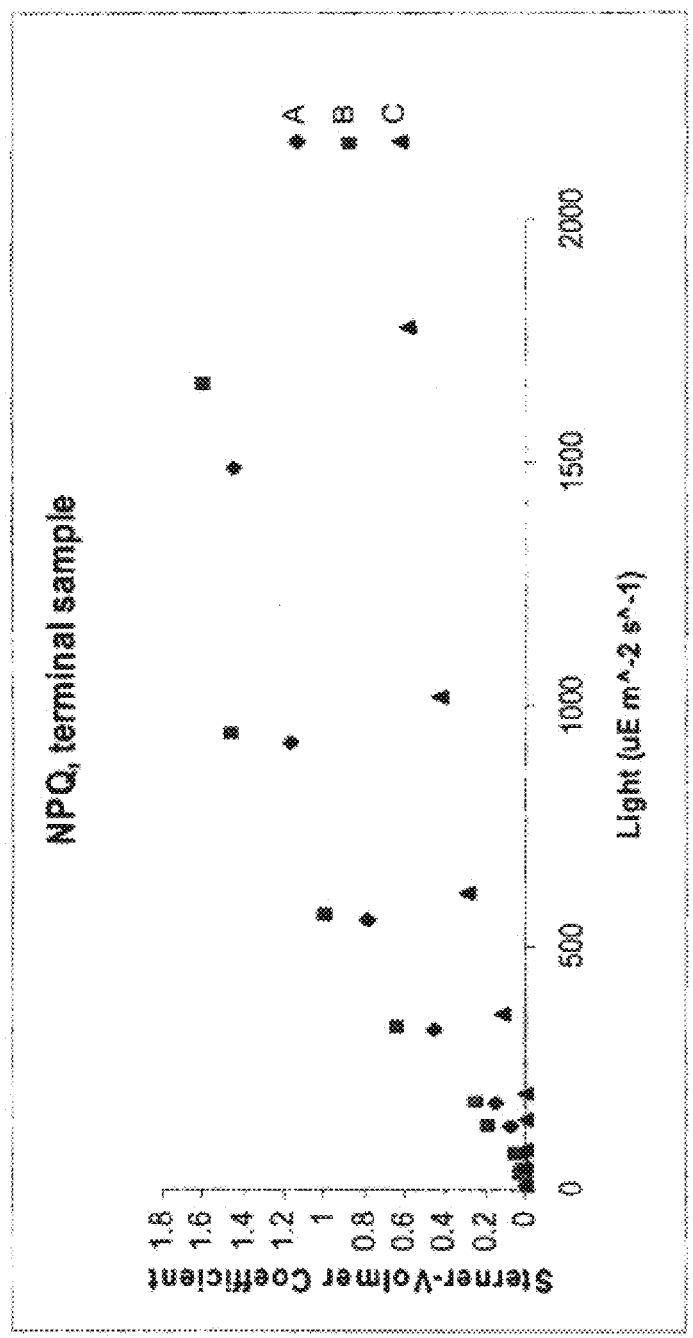

FIG. 4 shows non-photochemical quenching behavior for three algae samples. Algae samples A and B were grown using an illumination profile according to the invention. Illumination profile A was based on particle trajectories for an 840 $m^2$ raceway pond having a length to width ratio of 5.

Illumination profile B was based on particle trajectories for an 840 m² raceway pond having a length to width ratio of 19. The illumination profiles included 12 hours of simulated daylight and 12 hours of darkness. The particle trajectories were generated using computational fluid dynamics for model pond systems. Algae sample C corresponds to algae that were exposed to 24 hours of continuous light exposure at an intensity of about 41.5 µE. The total number of photons received by sample C during a 24 hour period were about ⅓ the total amount of photons received by samples A or B during a 24 hour period.

With regard to growth rate, algae samples A and B showed growth rates similar to the growth rates for the growth pond sample in Example 1. By contrast, the growth rate for sample C was nearly 3 times greater than either sample A or B (and therefore nearly 3 times greater than the growth pond sample in Example 1), in spite of sample C receiving only about ⅓ of the total number of photons. This indicates that the exposure conditions for sample C resulted in a much higher efficiency of photon use.

The algae in sample C also have qualitatively different behavior as compared to sample A or B, as shown in FIG. 4. After growing the algae samples, the algae samples were subjected to PAM fluorometry. Maximal and steady-state fluorescence signals were determined at levels of actinic light between 0 and 1750 µE/m²/s. In FIG. 4, the Stern-Volmer coefficient for the algae at various actinic light levels is shown. FIG. 4 shows that non-photochemical quenching processes are activated at lower levels of actinic light for the pond grown algae and the algae grown according to the invention. By contrast, the algae grown under a continuous light condition engage in less non-photochemical quenching.

Example 3

Configuration for Simulated Growth Vessel

Figure 5:
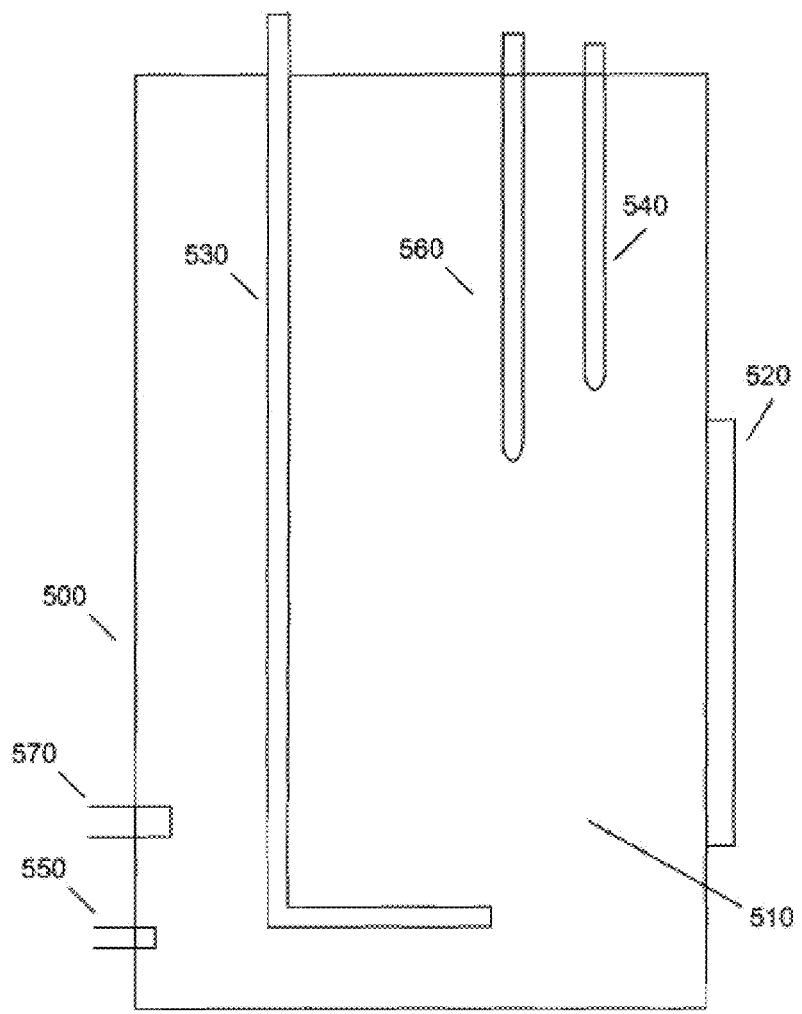
FIG. 5 schematically shows an example of vessel for algae growth according to an embodiment of the invention.

FIG. 5 shows an example of a vessel for holding algae-containing water for exposure to an illumination profile according to the invention. In FIG. 5, the vessel 500 is generally shown from a side view looking down on the cross-section of the vessel that can be illuminated by an illumination source. The vessel can include an interior volume 510 that holds the algae-containing water. Thermoelectric heater 520 is shown as attached to the side of vessel 500, but one or more heaters 520 can be attached to any convenient face of vessel 500. Aeration tube 530 provides a method for gas delivery and agitation within interior volume 510. Alternatively, an automated source of agitation can be used for agitating the contents of interior volume 510. Thermometer 540 allows for measurement of temperature in the interior volume 510. Alternatively, an aeration port 550 can provide an inlet for introduction of $CO_2$ as well as an outlet for excess oxygen in the interior volume. In some embodiments, aeration tube 530 and/or aeration port 550 can be omitted, if it is not desired to control $CO_2$ and/or $O_2$ concentration. Probe 560 can allow for measurement of pH, $O_2$, temperature, or other state variables within the interior volume. Port 570 can allow for addition or extraction of water from the interior volume 510.

Figure 6:
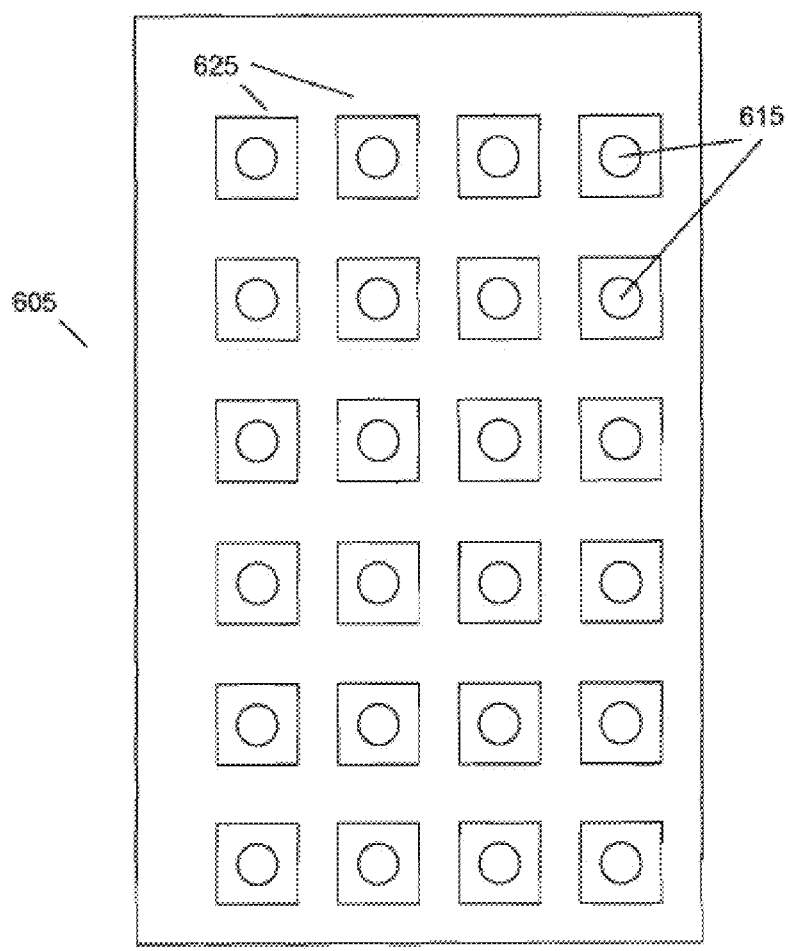
FIG. 6 schematically shows an example of an light source array according to an embodiment of the invention.

FIG. 6 shows an example of an illumination source 605 according to an embodiment of the invention. In FIG. 6, a plurality of LED light sources 615 are provided as part of an array. Each LED light source resides behind a lens 625. Lens 625 can convert the point source light emitted by a typical LED 615 into a focused beam of light. This can allow the majority of the light from an LED 615 to be incident on a desired area of a growth vessel. In FIG. 6, the LED light sources are shown as being in rows. Optionally, each LED 615 can be controlled independently to operate at a desired power, or each row of LEDs can receive the same power, or the entire array can receive the same power. Of course, other options for controlling LEDs in an array can also be used. Depending on the embodiment, it may be desirable to use multiple power sources to deliver power to the LEDs due to equipment constraints or other considerations. For example, it may be desirable to use equipment with a maximum amperage rating, so that only a few LEDs from an array are powered by any given power source.

Example 4

Process Overview

Figure 7:
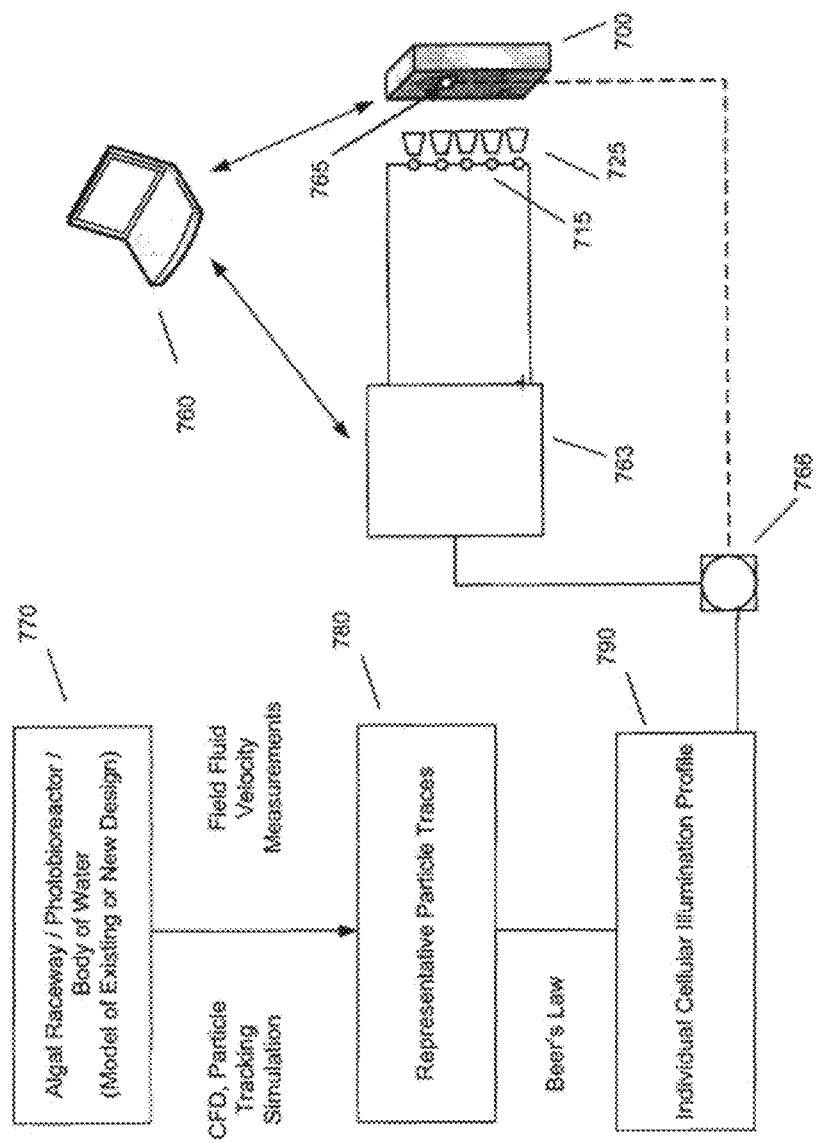
FIG. 7 shows an overview of a process according to an embodiment of the invention.

FIG. 7 shows an overview of a process according to an embodiment of the invention. In FIG. 7, a reference geometry 770 can be identified. The reference geometry 770 can be an existing algal raceway, photobioreactor, or other body of water. Alternatively, reference geometry 770 can be modeled using a computer. If reference geometry 770 represents an existing structure, fluid velocity measurements can be made to develop a fluid field model for flow in the reference geometry. Otherwise, computational fluid dynamics can be used to model fluid flow in the geometry. After developing a fluid flow model, representative particle traces or trajectories can be developed 780. In conjunction with an attenuation model such as Beer's law, the particle trajectories can be used to develop one or more illumination profiles 790.

In a working example, illumination profiles were developed for particle trajectories based on a model of an algal raceway. The algal raceway had a surface area of 840 m² and a depth of 30 cm. The algal raceway was mixed at 30 cm/sec. In order to develop parameters for determining an optical density, several values were determined. First, it was determined that a dense pond of N. gaditana contained about 14 milligrams of Chlorophyll a per gram of ash free dry weight (AFDW) algae. This was based on measurements from a raceway greenhouse pond similar to the pond described in Example 1. Next, an algae density of 0.3 g of ash free dry weight algae per liter was selected as a desired concentration for investigation. Next, a model for determining an extinction coefficient (optical density) as a function of algae concentration was determined based on linear regression of light attenuation and concentration data from a raceway greenhouse pond for N. gaditana. The resulting extinction coefficient model was (mg Chlorophyll a per g AFDW)*(g AFDW/liter)
*0.072+0.0112.

This calculated optical density could then be used in Beer's law to determine illumination intensities at various depths as a function of time to develop an illumination profile based on each desired trajectory.

In order to use an illumination profile 790, the system for exposing algae to illumination can be calibrated. One or more sensors 765 capable of measuring photosynthetically active radiation (PAR) can be placed on the surface of the vessel 700 for holding an algae sample. Constant current controller or voltage controller 763 can then be used to drive LEDs 715 at various power levels. The light from LEDs 715 can pass through lenses 725 which direct the light onto the surface of vessel 700. The one or more PAR sensors 765 can detect the amount of incident illumination at a given current level, and this information can be used to develop a calibration curve 766 for the LEDs 715. Based on calibration curve 766, the illumination profile 730 can be translated into current values for use in controller 763 in order to expose an algae sample to the desired profile. Optionally, controller 763 can be driven by a separate processor 760, or a processor in controller 763 can process the illumination profile data. Separate processor 760 can also optionally control other functions, such as a thermoelectric heater for controlling temperature in vessel 700.

For computing device 760, any convenient computing device may be used. The computing device 760 can correspond to a personal computer, a handheld computing device, a dedicated controller, or another type of computing device capable of receiving input corresponding to a profile and delivering output signals to control a corresponding device that generates the desired output. Optionally, the computing device 760 can control a thermoelectric heater, illumination device, or other device using one or more software programs installed on the computing device.

Example 5

Scale Down Simulations on Algal Strains of Five Taxonomic Classes

At least ten algal strains were cultured in greenhouse ponds and tested in the algal growth simulator system to compare productivities obtained by growth simulator cultures with pond cultures. The tested algal strains included a strain of the Eustigmatophyceae class, six strains characterized as species of the Trebouxiophyceae class; a mutagenized strain characterized as being a species of the Prasinophyceae class, a strain characterized as a species within the Chlorophyceae class, and a mutagenized strain characterized as being a species of the Coscinodiscophyceae. These strains were cultured in ponds using variations of F/2 algal culture medium, some of which were formulations lacking a nitrogen source (nitrogen deplete media). The mini-raceway ponds, with a surface area of 1.9 m$^2$, were constructed of fiberglass in the form of an oval with a central barrier to provide raceway-like culture flow conditions were outfitted with a single paddle wheel positioned at mid-run for culture mixing. The ponds received natural sunlight plus additional light supplementation for 16 hours per day supplied by two 1000 W metal halide lamp fixtures. Particle trajectories were calculated based on a fluid dynamic model of these ponds based on fluid velocimetry measurements.

Independently (and with different strains), light extinction profiles were empirically measured with a spherical light probe to measure PAR wavelengths across a depth profile (in these same mini-raceways) for nine algal strains. This was conducted for 22 cultures, each at multiple time points, to cover various phases of the culture's growth. These measurements incorporated both nutrient replete and nutrient deplete growth for the 9 distinct strains which covered multiple algal genera including members of the eustigmatophyceae, chlorophyceae, prasinophyceae, and trebouxiophyceae algal classes. This background data provided taxon-specific estimations for extinction coefficients which were used in scale-down modeling of raceway cultivation.

The ponds had a surface area of 1.9 m$^2$ and held a total of 200 liters of culture medium. Pond cultures were grown over a period of 7-12 days in typical experiments, where the initial culture density was approximately 0.05 to 0.1 OD at 730 nm. Over the course of an experiment, $OD_{730}$, total organic carbon (TOC), and fatty acid methyl esters (FAME) were measured daily from raceway cultures. Once logarithmic culture growth was observed to slow and begin to asymptote, the pond cultures were re-diluted. The $OD_{730}$ at which this occurred varied from strain to strain, and cultures reached densities ranging from an $OD_{730}$ of 0.3 to an $OD_{730}$ of 1.3. Both the temperature of the growth medium and light intensity (insolation) at the surface of the pond were measured continuously. These environmental insolation and temperature data were used in scale-down simulations to generate light and temperature profiles experienced by a typical algal cell during the course of that experiment.

For growth in the scaled-down simulator, these same algal strains were inoculated into 150 ml tissue culture flasks containing 100 mls of the same media as used in greenhouse experiments. The flasks had dimensions of 1.9 cm×7.8 cm×12.6 cm. The initial culture density was the same as the initial density of pond cultures, approximately 0.05 to 0.1 OD at 730 nm, and cultures were allowed to grow for an equivalent amount of time as the simulated pond cultures, but without dilution over the course of the culture period. The maximal $OD_{730}$ reached during the growth period varied from strain to strain, and ranged from approximately 0.6 to about 1.3. The scale-down simulations were not conducted contemporaneously with greenhouse experiments but were separated in time, in some cases by as much as a year. For each strain the insolation and temperature data collected at the time of raceway culturing were used in scale-down simulations. These environmental data in combination with [1]taxon-specific extinction coefficient profiles, [2]simulated particle trajectories, and [3]measurements of the scale-down cultures optical density were used to generate scale-down culture simulations. The flasks were maintained at the desired temperature by partial immersion in a programmable, temperature-controlled water bath. Flasks were positioned with the 7.8×12.6 cm plane facing a light source capable of producing light intensities up to 2000 μE/m$^2$/s PAR from an array of cool white (~6000K) LEDs. The depth of the scaled-down cultures (i.e., the light path through the culture medium) was 1.9 cm. Similar to the greenhouse ponds which were being modeled, triplicate cultures of each strain were sampled daily to obtain measurements of optical density ($OD_{730}$), TOC, and FAME. Daily, optical density values were measured for these experimental cultures and used to update the programming of the algal growth simulation to adjust the light profile based on attenuation as it would be predicted to occur in pond cultures having the same density as the growth flasks. The scale-down simulations were carried out for 7-9 days.

Total organic carbon was quantitated using a Shimadzu TOC-VCSH Analyzer and FAME was analyzed by organic extraction and gas chromatography using methods provided herein or modifications thereof.

Figures 8A, 8B:
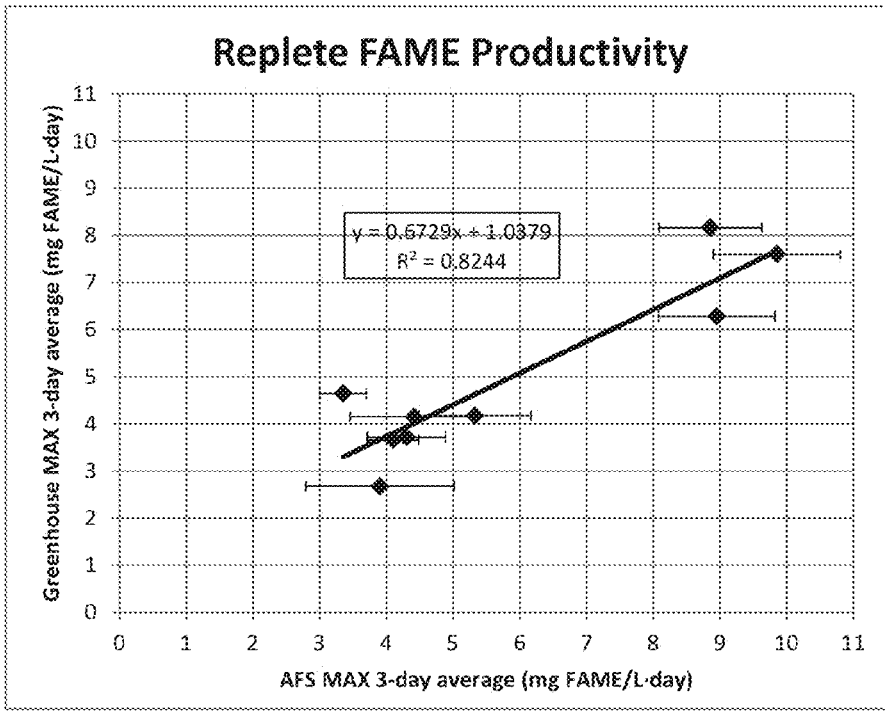
FIG. 8 shows graphs providing the correlations of the productivities between growth simulator (x-axis) and pond (y-axis) cultures of nine algal strains. Each data point is the highest averaged three day productivity for the strain. A) Lipid (FAME) productivities of strains in the growth simulator system are plotted against the lipid productivities of the same strains in greenhouse ponds. B) Total organic carbon productivities of nine strains in the growth simulator system are plotted against the total organic carbon productivities in greenhouse ponds.

For some strains, the values for daily growth and productivity observed at large scale (greenhouse) matched very closely with the results obtained in the scale-down simulation. For other strains, while the absolute values for biomass daily yields varied between pond cultures and scaled-down simulator cultures, the measured productivities (three day averages of the daily productivity, expressed as mg per liter per day) still matched quite closely. Additionally, for some strains there were significant deviations in measured productivities between pond cultures and growth simulator cultures that were observed during the first 24-48 hours of culture growth. For this reason, the productivity values obtained during the first 48 hours were not incorporated into running average calculations of productivity. A running 3-day average of productivity was calculated for each replicate simulator culture. The maximal 3-day average value measured for each culture was then used to calculate a mean and standard deviation for biological triplicates and these values are presented in FIG. 8. The data presented in FIG. 8 demonstrate a strong correlation between algal growth simulator ("AFS", x-axis) and pond ("Greenhouse", y-axis) culture productivity for both FAME ($R^2$=0.8244) and TOC ($R^2$=0.8601), validating the use of the scaled-down culture system provided here for exposing algal samples to illumination profiles to simulate pond conditions for assessing strain productivity.

During the course of testing these and additional strains in growth simulator cultures, the total absorptance through the flasks (($I_0$–I)/$I_0$, measured across all PAR wavelengths) was observed to be as high as 50%, as algal concentrations increased toward the end of the 7-9 day experiments, without having any discernible effect on the correlation of the productivities of the simulator cultures with greenhouse pond productivities.

Although the present invention has been described in terms of specific embodiments, it is not so limited. Suitable alterations/modifications for operation under specific conditions should be apparent to those skilled in the art. It is therefore intended that the following claims be interpreted as covering all such alterations/modifications as fall within the true spirit/scope of the invention.

What is claimed is:

1. A method for prediction of algal behavior in a reference environment based on growth of algae sample in a controlled environment, comprising:
    calculating a particle trajectory for a particle in a reference volume, the particle trajectory comprising at least a plurality of position values in the reference volume, the plurality of position values having associated times, the position values including at least a depth value relative to a surface of the reference volume;
    determining an illumination profile based on the particle trajectory by obtaining an illumination intensity corresponding to the plurality of position values and associated times, the determining an illumination profile comprising:
        selecting a depth value and an associated time;
        selecting an intensity of illumination that is incident on a surface of the reference volume at the associated time;
        determining an optical density for the reference volume at the associated time; and
        calculating an illumination for the selected depth value based on an attenuation of the selected incident illumination intensity and the determined optical density;
    exposing an algae sample comprising an algal strain in a vessel to light intensity corresponding to the illumination profile for a period of time corresponding to a sample culturing period, the algae sample in the vessel having a sample depth, a sample volume, and a sample absorbance, a product of the sample absorbance and the sample depth being less than about 10.0 cm, the sample volume being less than the reference volume; and
    characterizing at least one algae property for algae in the reference volume based on at least one measured algae property of the algae sample.

2. The method of claim 1, wherein calculating a particle trajectory comprises:
    measuring a velocity field for a fluid flow in the reference volume; and
    constructing a particle trajectory in the fluid flow using a stochastic process.

3. The method of claim 1, wherein calculating a particle trajectory comprises:
    modeling a fluid flow in the reference volume;
    simulating a plurality of particle traces in the modeled fluid flow in the reference volume; and
    constructing a particle trajectory based on a combination of one or more particle traces from the plurality of particle traces.

4. The method of claim 1, wherein the particle trajectory comprises a continuous function of locations within the reference volume, the continuous functions of locations being a function of time.

5. The method of claim 1, wherein said attenuation is calculated using one or more extinction coefficients for the algal strain of the algal sample ore at least one taxonomically related algal strain.

6. The method of claim 5, wherein said one or more extinction coefficients for the algal strain is a known or determined extinction coefficient for at least one taxonomically related algal strain, or is based a function or more empirically determined extinction coefficients for the algal strain.

7. The method of claim 1, wherein the illumination profile is modified during the sample culturing period.

8. The method of claim 1, further comprising determining a temperature profile at the associated times, the temperature profile being associated with at least one of the reference volume and the position values.

9. The method of claim 1, wherein the optical density $\alpha$ is defined by the equation $\alpha L = -\log_{10}(I_L/I_0)$, where $I_0$ represents an intensity of light incident at a surface and $I_L$ represents an intensity of light at distance L from the surface.

10. The method of claim 1, wherein characterizing at least one algae property for algae in the reference volume comprises:
    withdrawing at least a portion of the algae sample;
    measuring a property of the withdrawn algae sample;
    calculating an algae growth rate;
    selecting an initial algae concentration for the reference volume; and
    characterizing the at least one algae property in the reference volume based on a relationship between the initial algae concentration for the reference volume, an algae concentration for the vessel or the withdrawn algae sample, and the calculated algae growth rate.

11. The method of claim 10, wherein selecting an initial algae concentration for the reference volume comprises determining an initial algae concentration based on a selected optical density for the reference volume.

12. The method of claim 1, wherein the sample volume of the algae sample is less than about 25% of the reference volume.

13. The method of claim 1, wherein the at least one characterized algae property is biomass accumulation, ash free dry weight, or total organic carbon.

14. The method of claim 1, wherein the at least one characterized algae property is lipid accumulation, growth rate, or the ratio of variable fluorescence to maximal fluorescence ($F_v/F_m$).

15. The method of claim 1, wherein a product of the sample absorbance and the sample depth is less than about 4.0 cm.

16. The method of claim 1, wherein a product of the sample absorbance and the sample depth is less than about 1.0 cm.

17. The method of claim 1, wherein during the culturing period the sample absorbance is greater than about 0.3.

18. The method of claim 17, wherein during the culturing period the sample absorbance is at least about 0.45.

19. The method of claim 1, wherein the reference volume comprises a raceway pond.

20. A method for comparing an algal property of algae samples, comprising:

calculating a particle trajectory for a particle in a reference volume, the particle trajectory comprising at least a plurality of position values in the reference volume, the plurality of position values having associated times, the position values including at least a depth value relative to a surface of the reference volume;

determining an illumination profile based on the particle trajectory by obtaining an illumination intensity corresponding to the plurality of position values and associated times, the determining an illumination profile comprising:

selecting a depth value and an associated time;

selecting an intensity of illumination that is incident on a surface of the reference volume at the associated time;

determining an optical density for the reference volume at the associated time; and calculating an illumination for the selected depth value based on an attenuation of the selected incident illumination intensity and the determined optical density;

exposing a first algae sample of a first algal strain in a first vessel to light intensity corresponding to the illumination profile, the first algae sample in the first vessel having a first sample depth, a first sample volume, and a first sample absorbance, a product of the first sample absorbance and the first sample depth being less than about 10.0 cm, the first sample volume being less than the reference volume;

exposing a second algae sample of a second algal strain in a second vessel to light intensity corresponding to the illumination profile, the second algae sample in the second vessel having a second sample depth, a second sample volume, and a second sample absorbance, a product of the second sample absorbance and the second sample depth being less than about 10.0 cm, the second sample volume being less than the reference volume;

characterizing at least one algae property for the first algae sample;

characterizing the at least one algae property for the second algae sample; and comparing the characterized at least one algae property for the first algae sample and the characterized at least one algae property for the second algae sample.

21. The method of claim 20, wherein the algae property is biomass accumulation, lipid production, growth rate, or a photosynthetic property.

22. A method for comparing an algal property of algae samples, comprising:

calculating a particle trajectory for a particle in a reference volume, the particle trajectory comprising at least a plurality of position values in the reference volume, the plurality of position values having associated times, the position values including at least a depth value relative to a surface of the reference volume;

determining an illumination profile based on the particle trajectory by obtaining an illumination intensity corresponding to the plurality of position values and associated times, the determining an illumination profile comprising:

selecting a depth value and an associated time;

selecting an intensity of illumination that is incident on a surface of the reference volume at the associated time;

determining an optical density for the reference volume at the associated time; and calculating an illumination for the selected depth value based on an attenuation of the selected incident illumination intensity and the determined optical density;

exposing a first algae sample of a first algal strain in a first vessel to light intensity corresponding to the illumination profile, the first algae sample in the first vessel having a first sample depth, a first sample volume, and a first sample absorbance, a product of the first sample absorbance and the first sample depth being less than about 10.0 cm, the first sample volume being less than the reference volume;

exposing a second algae sample of a second algal strain in a second vessel to light intensity corresponding to the illumination profile, the second algae sample in the second vessel having a second sample depth, a second sample volume, and a second sample absorbance, a product of the second sample absorbance and the second sample depth being less than about 10.0 cm, the second sample volume being less than the reference volume, and at least one environmental factor of the second vessel being different from a corresponding at least one environmental factor of the first vessel;

characterizing at least one algae property for the first algae sample;

characterizing the at least one algae property for the second algae sample; and comparing the characterized at least one algae property for the first algae sample and the characterized at least one algae property for the second algae sample to determine the comparative effect of the at least one environmental factor.

23. The method of claim 22, wherein the at least one environmental factor that is different for the first algae sample and the second algae sample is a speed of mixing, a presence of a mixing structure, a presence of mixing jets, a $CO_2$ concentration, an $O_2$ concentration, a pH, an algae sample depth, a temperature, or a combination thereof.

24. The method of claim 22, wherein the first vessel and the second vessel are the same, the method further comprising:

removing the first algae sample from the vessel after the exposure of the first algae sample to the illumination profile; and introducing the second algae sample into the vessel.

25. The method of claim 22, wherein the first algae sample comprises a first algae strain and the second algae sample comprises a second algae strain.

26. The method of claim 22, wherein comparing the characterized at least one algae property for the first algae sample and the characterized at least one algae property for the second algae sample comprises:

measuring one or more algae properties for the first algae sample;

measuring the one or more algae properties for the second algae sample;

characterizing the at least one algae property for the first algae sample based on the measured one or more algae properties for the first algae sample; and characterizing the at least one algae property for the second algae sample based on the measured one or more algae properties for the second algae sample.

* * * * *